United States Patent
Rasmussen et al.

(10) Patent No.: US 10,954,533 B2
(45) Date of Patent: *Mar. 23, 2021

(54) PROCESSES OF PRODUCING FERMENTATION PRODUCTS

(71) Applicant: NOVOZYMES A/S, Bagsvaerd (DK)

(72) Inventors: Thomas Rasmussen, Bagsvaerd (DK); Jeremy Saunders, Franklinton, NC (US); James Croonenberghs, Franklinton, NC (US); Zhengfang Kang, Franklinton, NC (US); Joyce Craig, Franklinton, NC (US); Michael John Akerman, Franklinton, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/440,623

(22) Filed: Jun. 13, 2019

(65) Prior Publication Data

US 2019/0323041 A1  Oct. 24, 2019

Related U.S. Application Data

(60) Continuation of application No. 15/822,352, filed on Nov. 27, 2017, now Pat. No. 10,364,445, which is a division of application No. 14/388,595, filed as application No. PCT/US2013/034337 on Mar. 28, 2013, now Pat. No. 9,856,498.

(60) Provisional application No. 61/617,799, filed on Mar. 20, 2012.

(51) Int. Cl.
| | |
|---|---|
| *C12P 7/02* | (2006.01) |
| *C12P 7/04* | (2006.01) |
| *C12P 7/40* | (2006.01) |
| *C12P 7/16* | (2006.01) |
| *C12N 9/30* | (2006.01) |
| *C12P 7/14* | (2006.01) |
| *C12P 7/06* | (2006.01) |
| *C12P 19/14* | (2006.01) |
| *C12N 9/42* | (2006.01) |

(52) U.S. Cl.
CPC .............. *C12P 7/14* (2013.01); *C12N 9/2445* (2013.01); *C12P 7/06* (2013.01); *C12P 19/14* (2013.01); *Y02E 50/10* (2013.01)

(58) Field of Classification Search
CPC .... C12P 19/14; C12P 9/42; C12P 7/14; C12P 7/06
See application file for complete search history.

(56) References Cited

U.S. PATENT DOCUMENTS

| | | | |
|---|---|---|---|
| 5,231,017 A | 7/1993 | Lantero | |
| 7,541,026 B2 | 6/2009 | Power | |
| 7,641,928 B2 | 1/2010 | Jump | |
| 8,338,121 B2 | 12/2012 | Sweeney | |
| 8,541,651 B2 | 9/2013 | Wogulis | |
| 10,041,054 B2 | 8/2018 | Deinhammer | |
| 2004/0115779 A1 | 6/2004 | Olsen | |
| 2004/0234649 A1 | 11/2004 | Lewis | |
| 2005/0100996 A1 | 5/2005 | Lantero, Jr. | |
| 2008/0138871 A1 | 6/2008 | Smith | |
| 2011/0171674 A1 | 7/2011 | Lopes-Ferreira et al. | |
| 2013/0217079 A1 | 8/2013 | Wogulis | |
| 2014/0080183 A1 | 3/2014 | Dieker | |
| 2014/0315243 A1 | 10/2014 | Deinhammer | |

FOREIGN PATENT DOCUMENTS

| | | |
|---|---|---|
| EP | 1916308 A1 | 4/2008 |
| JP | 04004888 A1 | 1/1992 |
| WO | 92/20777 A1 | 11/1992 |
| WO | 97/038111 A1 | 10/1997 |
| WO | 01/60752 A1 | 8/2001 |
| WO | 01/62947 A1 | 8/2001 |
| WO | 02/38787 A2 | 5/2002 |
| WO | 2004/80923 A2 | 9/2004 |
| WO | 2005/074656 A2 | 8/2005 |
| WO | 2007/56321 A1 | 5/2007 |
| WO | 2007/076388 A2 | 7/2007 |
| WO | 2008/23060 A1 | 2/2008 |
| WO | 2009/121058 A1 | 10/2009 |
| WO | 2009/148945 A1 | 12/2009 |
| WO | 2010/128140 A1 | 11/2010 |
| WO | 2011/072191 A2 | 6/2011 |
| WO | 2011/080352 A1 | 7/2011 |
| WO | 2011/126897 A2 | 10/2011 |
| WO | 2012/109119 A2 | 8/2012 |
| WO | 2012/149275 A1 | 11/2012 |
| WO | 2013/148993 A1 | 10/2013 |
| WO | 2013/166405 A2 | 11/2013 |
| WO | 13/181760 A1 | 12/2013 |
| WO | 2005/113785 A2 | 12/2013 |
| WO | 14/028434 A2 | 2/2014 |
| WO | 14/092960 A1 | 6/2014 |
| WO | 14/093123 A1 | 6/2014 |
| WO | 14/093125 A1 | 6/2014 |
| WO | 14/099415 A1 | 6/2014 |
| WO | 2015/035914 A1 | 3/2015 |
| WO | 15/065978 A1 | 5/2015 |

OTHER PUBLICATIONS

Basu et al, 2006, Biochim Biophys Acta 1760(2), 134-140.
Chung et al, 1985, Biotechnol Bioeng 27, 308-315.
Galand, 1986, Comp Biochem Physiol, 85A(1), 109-115.
Horikoshi et al, 1989, WPI Access No. 1989-304909.
Horikoshi et al, 1992, WPI Access No. 1992-060502.
Lynd et al, 2002, Microbiol Bol Biol Revs 66(3), 506-577.
Morita, 1987, WPI Access No. 1987-059541.
Soni, 2007, Microbes Section 4-6-5, 336.
Thevelein et al, 1995, Trends Biochem Sci 20(1), 3-10.
Fedrova et al, 2010, UniprotKB Accession No. A1CR85.

(Continued)

*Primary Examiner* — Maryam Monshipouri
(74) *Attorney, Agent, or Firm* — David Fazzolare

(57) ABSTRACT

The invention relates to processes of producing a fermentation product, comprising liquefying a starch containing material with an alpha-amylase; pre-saccharifying and/or saccharifying and fermenting using a fermentation organism in the presence of a carbohydrate source generating enzyme and a cellulolytic composition The invention also relates to methods of dewatering whole stillage.

12 Claims, 4 Drawing Sheets

Specification includes a Sequence Listing.

(56) References Cited

OTHER PUBLICATIONS

Fedrova et al, 2010, UniprotKB Accession No. A1D51.
Martinez et al, 2011, UniProt, Accession No. G0RRG0.
Adav et al, Mol Cell Prot 11.7, 1-15.
Juhasz et al, Process Bio, 40, 3519-3525.
Thomas 2009, Washington U PhD Thesis.

PROCESSES OF PRODUCING FERMENTATION PRODUCTS

CROSS-REFERENCE TO RELATED APPLICATIONS

This application is a continuation of U.S. application Ser. No. 15/822,352 filed Nov. 27, 2017, now U.S. Pat. No. 10,364,445, which is a division of U.S. application Ser. No. 14/388,595 filed Sep. 26, 2014, now U.S. Pat. No. 9,856,498, which is a 35 U.S.C. 371 national application of PCT/US2013/034337 filed Mar. 28, 2013, which claims priority or the benefit under 35 U.S.C. 119 of U.S. provisional application No. 61/617,799 filed Mar. 30, 2012, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to processes of producing fermentation products from starch-containing material using a fermenting organism. The invention also relates to methods of dewatering whole stillage.

BACKGROUND OF THE INVENTION

A vast number of commercial products that are difficult to produce synthetically are today produced by fermenting organisms. Such products include alcohols (e.g., butanol, ethanol, methanol, 1,3-propanediol); organic acids (e.g., acetic acid, citric acid, gluconate, gluconic acid, itaconic acid, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones. Fermentation is also commonly used in the consumable alcohol (e.g., beer and wine), dairy (e.g., in the production of yogurt and cheese), leather, and tobacco industries. A vast number of processes of producing fermentation products, such as ethanol, by fermentation of sugars provided by degradation of starch-containing materials are known in the art. However, production of fermentation products, such as ethanol, from such starch-containing material is still too costly. Therefore, there is a need for providing processes that can increase the yield of the fermentation product and thereby reduce the production costs. It is an object of the present invention to provide improved processes for producing fermentation products.

SUMMARY OF THE INVENTION

The present invention relates to processes of producing fermentation products from starch-containing material using a fermenting organism.

In the first aspect, the invention relates to processes of producing fermentation products, comprising
(a) liquefying a starch-containing material with an alpha-amylase;
optionally pre-saccharifying the liquefied material before step (b);
(b) saccharifying the liquefied material;
(c) fermenting using a fermentation organism;
wherein a carbohydrate-source generating enzyme and/or a cellulolytic composition are present or added during the optional presaccharification step, saccharification step (b), and/or fermentation step (c), or simulataneous saccharification and fermentation.

The cellulolytic composition may be derived from *Trichoderma reesei, Humicola insolens* or *Chrysosporium lucknowense*. The cellulolytic composition comprises a beta-glucosidase, a cellobiohydrolase, and an endoglucanase. In a preferred embodiment the cellulolytic composition comprises a beta-glucosidase having a Relative ED50 loading value of less than 1.00, preferably less than 0.80, such as preferably less than 0.60, such as between 0.1-0.9, such as between 0.2-0.8, such as 0.30-0.70. The Relative ED50 loading value is determined relative to the ED50 for the *Aspergillus fumigatus* beta-glucosidase shown in SEQ ID NO: 6 herein. Example 3 described how to on determining the Relative ED50 loading value for beta-glucosidases.

The cellulolytic composition may comprise some hemicellulase, such as, e.g., xylanase and/or beta-xylosidase. The hemicellulase may come from the cellulolytic composition producing organism or from other sources, e.g., the hemicellulase may be foreign to the cellulolytic composition producing organism, such as, e.g., *Trichoderma reesei*. In a preferred embodiment the hemicellulase content in the cellulolytic composition constitutes less than 10 wt. % such as less than 5 wt. % of the cellulolytic composition.

In an embodiment the carbohydrate-source generating enzyme, preferably a glucoamylase, and the cellulolytic composition are added during a pre-saccharification step before simultaneous or sequential saccharification and fermentation.

The carbohydrate-source generating enzyme, such as a glucoamylase, is preferably a glucoamylase comprising side-activity of alpha-amylase, e.g., a thermostable variant of the alpha-amylase from *Rhizomucor pusillus* with *Aspergillus niger* glucoamylase linker and starch-binding domain (SBD) (SEQ ID NO: 11 herein). Specifically contemplated glucoamylases and alpha-amylase are described in the "Enzymes" sections below and in the Examples.

In a preferred embodiment the cellulolytic composition comprising a beta-glucosidase variant of the *Aspergillus fumigatus* beta-glucosidase shown in SEQ ID NO: 6 herein, which comprises one or more substitutions selected from the group consisting of L89M, G91L, F100D, I140V, I186V, S283G, N456E, and F512Y. In a preferred embodiment the *Aspergillus fumigatus* beta-glucosidase is a variant with any following substitutions:
F100D+S283G+N456E+F512Y;
L89M+G91L+I186V+I140V;
I186V+L89M+G91L+I140V+F100D+S283G+N456E+F512Y (using SEQ ID NO: 6 for numbering).

In a preferred embodiment the cellulolytic composition is derived from *Trichoderma reesei* and further comprising one or more of:
(i) an *Aspergillus fumigatus* cellobiohydrolase I, preferably the one shown in SEQ ID NO: 2 herein;
(ii) an *Aspergillus fumigatus* cellobiohydrolase II, preferably the one shown in SEQ ID NO: 4 herein;
(iii) an *Aspergillus fumigatus* beta-glucosidase variant thereof with the following substitutions: F100D, S283G, N456E, F512Y (using SEQ ID NO: 6 herein for numbering).

In a further embodiment of a process of the invention a trehalase is present or added during presacharification, simultaneous or sequential saccharification and fermentation. As shown in Example 5, combining a glucoamylase, a cellulolytic composition and a treahalase increases the ethanol yield."

Further, it was also found that processes of the invention result in backend (after recovery of the fermentation product, such as ethanol) benefits. After fermentation the fermentation product may be recovered, preferably by distillation, by separate the fermentation material into a liquid fraction (i.e., fermentation product), such as ethanol, and a solid fraction (i.e., whole stillage). After recovery of the fermentation product, the solid fraction (i.e., whole stillage) may be dewatered and separated into a solid phase (i.e., wet cake) and a liquid phase (Thin Stillage), e.g., by centrifugation. As shown in Example 6 improved dewatering is obtained.

In an embodiment the process of producing fermentation products of the invention, comprising:
(a) liquefying a starch containing material with an alpha-amylase;
(b) saccharifying the liquefied material using a carbohydrate-source generating enzyme;
(c) fermenting using a fermentation organism in the presence of a cellulolytic composition further comprising one or more polypeptides selected from the group consisting of:
GH61 polypeptide having cellulolytic enhancing activity;
beta-glucosidase;
Cellobiohydrolase I;
Cellobiohydrolase II;
or a mixture of two, three, or four thereof. In a preferred embodiment the cellulolytic composition is dosed from 0.01-0.1 mg EP/g DS.

The trehalase may be present or added in an amount of 5-1,000 micro g/g DS, such as 7-500 micro g/g DS, such as 10-250 micro g/g DS.

In the second aspect the invention relates to processes of producing a fermentation product, comprising
(a) saccharifying the liquefied material using a carbohydrate source generating enzyme and cellulolytic composition;
(b) fermenting using a fermentation organism.

The cellulolytic composition may be derived from *Trichoderma reesei, Humicola insolens* or *Chrysosporium lucknowense*. The cellulolytic composition comprising a beta-glucosidase, a cellobiohydrolase, and an endoglucanase. In a preferred embodiment the cellulolytic composition comprises a beta-glucosidase having a Relative ED50 loading value of less than 1.00, preferably less than 0.80, such as preferably less than 0.60, such as between 0.1-0.9, such as between 0.2-0.8, such as 0.30-0.70.

The cellulolytic composition may comprise some hemicellulase, such as, e.g., xylanase and/or beta-xylosidase. However, in a preferred embodiment the hemicellulase content in the cellulolytic composition constitutes less than 10 wt. % such as less than 5 wt. % of the cellulolytic composition.

In a preferred embodiment the cellulolytic composition comprises a beta-glucosidase variant of the *Aspergillus fumigatus* beta-glucosidase shown in SEQ ID NO: 6 herein, which comprises one or more substitutions selected from the group consisting of L89M, G91L, F100D, I140V, I186V, S283G, N456E, and F512Y. In a preferred embodiment the *Aspergillus fumigatus* beta-glucosidase is a variant with any of the following substitutions:
F100D+S283G+N456E+F512Y;
L89M+G91L+I186V+I140V;
I186V+L89M+G91L+I140V+F100D+S283G+N456E+F512Y (using SEQ ID NO: 6 for numbering).

In a preferred embodiment the cellulolytic composition is derived from *Trichoderma reesei* and further comprises one or more of:
(i) an *Aspergillus fumigatus* cellobiohydrolase I, preferably the one shown in SEQ ID NO: 2 herein;
(ii) an *Aspergillus fumigatus* cellobiohydrolase II, preferably the one shown in SEQ ID NO: 4 herein;
(iii) an *Aspergillus fumigatus* beta-glucosidase variant thereof with the following substitutions: F100D, S283G, N456E, F512Y (using SEQ ID NO: 6 herein for numbering).

In an embodiment the process of producing fermentation products comprising:
(i) saccharifying a starch-containing material with a carbohydrate-source generating enzyme at a temperature below the initial gelatinization temperature; and
(ii) fermenting using a fermentation organism in the presence of a cellulolytic composition further comprising one or more polypeptides selected from the group consisting of:
GH61 polypeptide having cellulolytic enhancing activity;
beta-glucosidase;
Cellobiohydrolase I;
Cellobiohydrolase II;
or a mixture of two, three, or four thereof.

In a preferred embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

In an third aspect the invention relates to methods of dewatering whole stillage derived from process of the invention. The methods of dewatering whole stillage comprises
(a) liquefying a starch-containing material with an alpha-amylase;
optionally pre-saccharifying the liquefied material before step (b);
(b) saccharifying the liquefied material;
(c) fermenting using a fermentation organism;
(d) separating the fermented material into a fermentation product and whole stillage;
(e) dewatering the whole stillage;
wherein a carbohydrate-source generating enzyme and/or a cellulolytic composition are present or added during the optional presaccharification step, saccharification step (b), and/or fermentation step (c), or simulataneous saccharification and fermentation.

In an embodiment the fermentation product is recovered from the fermented material by distillation or in another well-known way.

In an embodiment the dewatered whole stillage is separated into a liquid fraction (thin stillage) and a solid fraction (wet cake) which is dried and typically used for animal feed.

The enzymes used in a dewatering method of the invention are as disclosed in connection with the process of producing a fermentation product of the invention. Further, it is also contemplated to add the cellulolytic composition directly to the whole stillage to obtain improved dewatering. Therefore, in one aspect, the invention relates to methods of dewatering whole stillage comprising the steps of:
i) subjecting whole stillage to a cellulolytic composition defined in accordance with the present process of the invention,
ii) separating the material into a solid fraction and a liquid fraction.

Definitions

Enzymes:
Cellulolytic enzyme, cellulolytic composition, or cellulase: The term "cellulolytic enzyme", "cellulolytic composition", or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman N21 filter paper, microcrystalline cellulose, bacterial cellulose, algal cellulose, cotton, pretreated lignocellulose, etc. The most common total cellulolytic activity assay is the filter paper assay using Whatman N21 filter paper as the substrate. The assay was established by the International Union of Pure and Applied Chemistry (IUPAC) (Ghose, 1987, Measurement of cellulase activities, *Pure Appl. Chem.* 59: 257-68).

Cellulolytic enzyme activity is determined by measuring the increase in hydrolysis of a cellulosic material by cellulolytic enzyme(s) under the following conditions: 1-50 mg of cellulolytic enzyme protein/g of cellulose in Pretreated Corn Stover ("PCS") (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, Biochem. J. 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5L (Novozymes A/S, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptide having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose.

For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, Biochem. Soc. Trans. 26: 173-178).

Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components.

Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. Current Opinion In Microbiology, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, Pure & Appl. Chem. 59: 1739-1752, at a suitable temperature, e.g., 50° C., 55° C., or 60° C., and pH, e.g., 5.0 or 5.5.

Alpha-Amylases (alpha-1,4-glucan-4-glucanohydrolases, EC 3.2.1.1) are a group of enzymes, which catalyze the hydrolysis of starch and other linear and branched 1,4-glucosidic oligo- and polysaccharides.

Glucoamylases (glucan 1,4-alpha-glucosidase, EC 3.2.1.3) are a group of enzymes, which catalyze the hydrolysis of terminal (1→4)-linked α-D-glucose residues successively from non-reducing ends of the chains with release of beta-D-glucose.

Other Definitions

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Fragment: The term "fragment" means a polypeptide having one or more (e.g., several) amino acids absent from the amino and/or carboxyl terminus of a mature polypeptide main; wherein the fragment has enzyme activity. In one aspect, a fragment contains at least 85%, e.g., at least 90% or at least 95% of the amino acid residues of the mature polypeptide of an enzyme.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide of an *A. fumigatus* cellobiohydrolase I is amino acids 27 to 532 of SEQ ID NO: 2 based on the SignalP program (Nielsen et al., 1997, *Protein Engineering* 10: 1-6) that predicts amino acids 1 to 26 of SEQ ID NO: 2 are a signal peptide. In another aspect, the mature polypeptide of an *A. fumigates* cellobiohydrolase II is amino acids 20 to 454 of SEQ ID NO: 4 based on the SignalP program that predicts amino acids 1 to 19 of SEQ ID NO: 4 area signal peptide. In another aspect, the mature polypeptide of an *A. fumigatus* beta-glucosidase is amino acids 20 to 863 of SEQ ID NO: 6 based on the SignalP program that predicts amino acids 1 to 19 of SEQ ID NO: 6 are a signal peptide. In another aspect, the mature polypeptide of a *Penicillium* sp. GH61 polypeptide is amino acids 26 to 253 of SEQ ID NO: 8 based on the SignalP program that predicts amino acids 1 to 25 of SEQ ID NO: 8 are a signal peptide. In another aspect, the mature polypeptide of an *A. fumigatus* xylanase I is amino acids 18 to 364 of SEQ ID NO: 10 based on the SignalP program that predicts amino acids 1 to 17 of SEQ ID NO: 10 are a signal peptide. In another aspect, the mature polypeptide of a *T. reesei* cellobiohydrolase I is amino acids 18 to 514 of SEQ ID NO: 18 based on the SignalP program that predicts amino acids 1 to 17 of SEQ ID NO: 18 are a signal peptide. In another aspect, the mature polypeptide of a *T. reesei* cellobiohydrolase II is amino acids 19 to 471 of SEQ ID NO: 20 based on the SignalP program that predicts amino acids 1 to 18 of SEQ ID NO: 20 are a signal peptide. In another aspect, the mature polypeptide of a *T. reesei* beta-glucosidase is amino acids 20 to 744 of SEQ ID NO: 22 based on the SignalP program that predicts amino acids 1 to 19 of SEQ ID NO: 22 are a signal peptide.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity. In one aspect, the mature polypeptide coding sequence of an *A. fumigatus* cellobiohydrolase I is nucleotides 79 to 1596 of SEQ ID NO: 1 herein or the cDNA sequence thereof based on the SignalP program (Nielsen et al., 1997, supra) that predicts nucleotides 1 to 78 of SEQ ID NO: 1 herein encode a signal peptide. In another aspect, the mature polypeptide coding sequence of an *A. fumigatus* cellobiohydrolase II is nucleotides 58 to 1700 of SEQ ID NO: 3 herein or the cDNA sequence thereof based on the SignalP program that predicts nucleotides 1 to 57 of SEQ ID NO: 3 herein encode a signal peptide. In another aspect, the mature polypeptide coding sequence of an *A. fumigatus* beta-glucosidase is nucleotides 58 to 2580 of SEQ ID NO: 5 herein or the cDNA sequence thereof based on the SignalP program that predicts nucleotides 1 to 57 of SEQ ID NO: 5 herein encode a signal peptide. In another aspect, the mature polypeptide coding sequence of a *Penicillium* sp. GH61 polypeptide is nucleotides 76 to 832 of SEQ ID NO: 7 herein or the cDNA sequence thereof based on the SignalP program that predicts nucleotides 1 to 75 of SEQ ID NO: 7 herein encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Parent Enzyme: The term "parent" means an enzyme to which an alteration is made to produce a variant. The parent may be a naturally occurring (wild-type) polypeptide or a variant thereof.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Subsequence: The term "subsequence" means a polynucleotide having one or more (e.g., several) nucleotides absent from the 5' and/or 3' end of a mature polypeptide coding sequence; wherein the subsequence encodes a fragment having enzyme activity. In one aspect, a subsequence contains at least 85%, e.g., at least 90% or at least 95% of the nucleotides of the mature polypeptide coding sequence of an enzyme.

Variant: The term "variant" means a polypeptide having enzyme or enzyme enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Wild-Type Enzyme: The term "wild-type" enzyme means an enzyme expressed by a naturally occurring microorganism, such as a bacterium, yeast, or filamentous fungus found in nature.

DETAILED DESCRIPTION OF THE INVENTION

Figure 1:
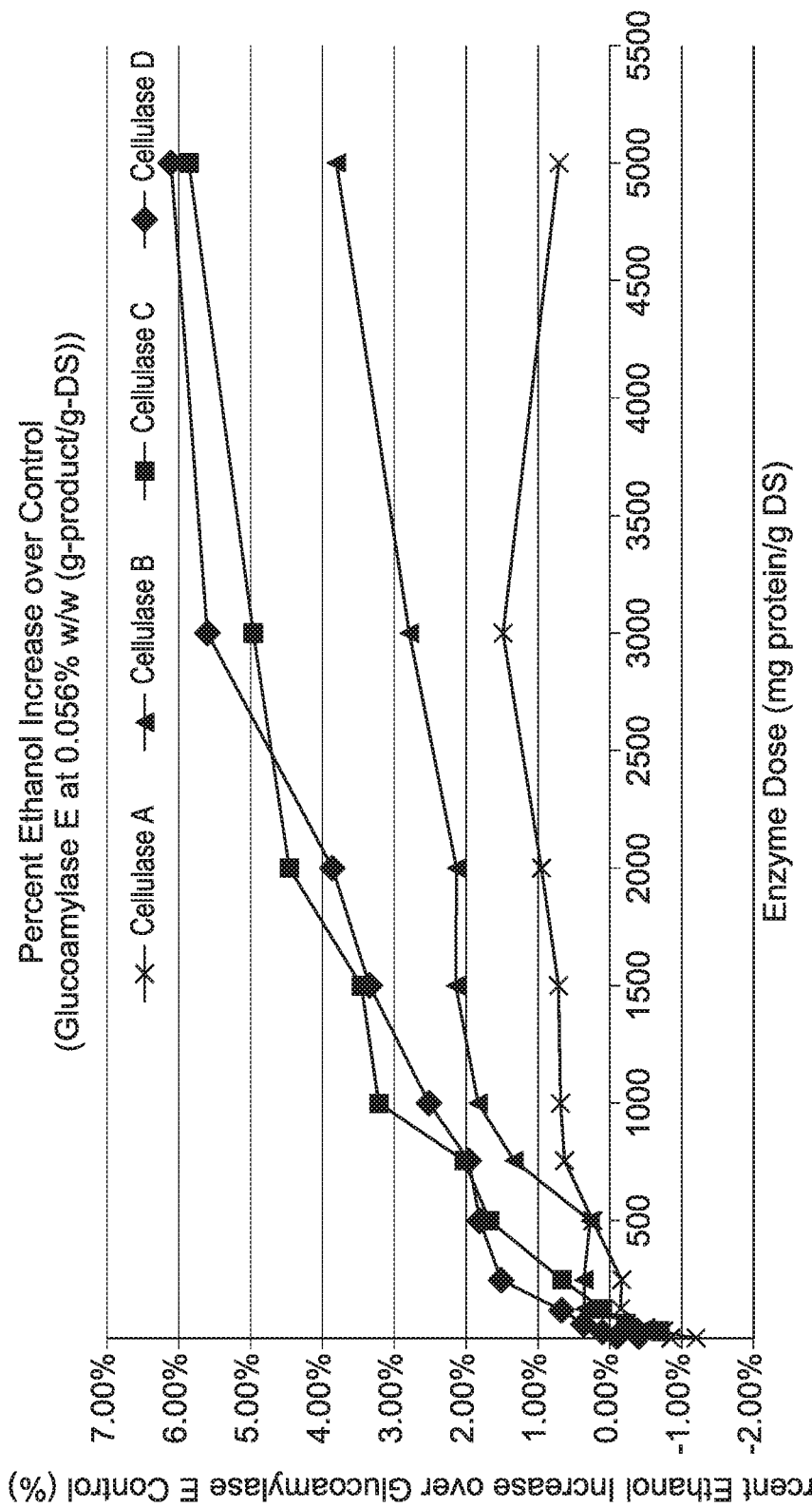
FIG. 1 shows a comparison of the ethanol yield when using four different cellulolytic composition (i.e., Cellulases A, B, C and D) during fermentation together with a glucoamylase.

The present invention relates to processes of producing fermentation products from gelatinized and ungelatinized starch-containing materials using a cellulolytic composition during presaccharification, simultaneous or sequential saccharification and fermentation. The invention also relates to methods of dewatering whole stillage derived from process of the invention.

The inventors have found that cellulolytic compositions developed for hydrolyzing lignocellulosic feed stocks give significantly increased ethanol yields when applied on liquefied corn mash (i.e., liquefied starch-containing materials) during presaccharification, and/or simultaneous saccharification and fermentation together with glucoamylase at concentrations significantly lower than the 3 to 10 milligram EP/g cellulose dosing used for hydrolyzing lignocellulosic feed stocks (e.g., pretreated corn stover).

The inventors also found that having a trehalase present or added during presacharification, and/or simultaneous saccharification and fermentation increases the ethanol yield.

Processes of the invention also result in backend benefits. It was found that improved dewatering of the whole stillage can be obtained when carrying out a process or method of the invention or by adding the cellulolytic composition directly to the whole stillage. Further, when adding a protease, such as one derived from *Thermoascus aurantiacus* (SEQ ID NO: 13) together with the carbohydrate source generating enzymes and cellulolytic composition during presaccharification, saccharification, and/or fermentation, such as simultaneous saccharification and fermentation (SSF), improved oil extraction from the whole stillage is obtained.

Processes for Producing Fermentation Products from Gelatinized Starch-Containing Materials In this aspect, the invention relates to processes of producing fermentation products, comprising
(a) liquefying a starch-containing material with an alpha-amylase;
optionally pre-saccharifying the liquefied material before step (b);
(b) saccharifying the liquefied material;
(c) fermenting using a fermentation organism;
wherein a carbohydrate-source generating enzyme and/or a cellulolytic composition are present or added during the optional presaccharification step, saccharification step (b), and/or fermentation step (c), or simulataneous saccharification and fermentation.

The cellulolytic composition may be derived from *Trichoderma reesei*, *Humicola insolens* or *Chrysosporium lucknowense*. The cellulolytic composition comprises a beta-glucosidase, a cellobiohydrolase, and an endoglucanase. In a preferred embodiment the cellulolytic composition comprises a beta-glucosidase having a Relative ED50 loading value of less than 1.00, preferably less than 0.80, such as preferably less than 0.60, such as between 0.1-0.9, such as between 0.2-0.8, such as 0.30-0.70.

The cellulolytic composition may comprise some hemicellulase, such as, e.g., xylanase and/or beta-xylosidase. The hemicellulase may come from the cellulolytic composition producing organism or from other sources, i.e., the hemicellulase may be foreign to the cellulolytic composition producing organism, such as, e.g., *Trichoderma reesei*.

In a preferred embodiment the hemicellulase content in the cellulolytic composition constitutes less than 10 wt. % such as less than 5 wt. % of the cellulolytic composition.

In an embodiment the carbohydrate-source generating enzyme, preferably a glucoamylase, and the cellulolytic composition are added during a pre-saccharification step carried out before simultaneous saccharification and fermentation.

In a preferred embodiment the carbohydrate-source generating enzyme is a glucoamylase, preferably a combination of glucoamylase and alpha-amylase.

Examples of suitable carbohydrate-source generating enzymes, preferably a glucoamylase, and alpha-amylase are disclosed below in the "Carbohydrate-Source Generating Enzymes (Saccharifying Enzymes)"—section and "Alpha-amylases" section and the Examples.

The carbohydrate-source generating enzyme, preferably a glucoamylase, is preferably a glucoamylase comprising side-activity of alpha-amylase, e.g., a thermostable variant of the alpha-amylase from *Rhizomucor pusillus* with *Aspergillus niger* glucoamylase linker and starch-binding domain (SBD) (SEQ ID NO: 11 herein).

In a specific embodiment the the carbohydrate source generating enzyme is a blend of glucoamylase derived from *Talaromyces emersonii* disclosed in WO 99/28448 or SEQ ID NO: 9 herein, *Trametes cingulata* glucoamylase disclosed as SEQ ID NO: 2 in WO 06/69289 or SEQ ID NO: 10 herein, and *Rhizomucor pusillus* alpha-amylase with *Aspergillus niger* glucoamylase linker and SBD disclosed as V039 in Table 5 in WO 2006/069290 or SEQ ID NO: 11 herein. The ration between the components may preferably be around 65:15:1.

In an embodiment the alpha-amylase is the *Rhizomucor pusillus* alpha-amylase having an *Aspergillus niger* glucoamylase linker and starch-binding domain (SBD) (SEQ ID NO: 11 herein) which further comprises at least one of the following substitutions or combinations of substitutions: D165M; Y141W; Y141R; K136F; K192R; P224A; P224R; S123H+Y141W; G20S+Y141W; A76G+Y141W; G128D+ Y141W; G128D+D143N; P219C+Y141W; N142D+ D143N; Y141W+K192R; Y141W+D143N; Y141W+ N383R; Y141W+P219C+A265C; Y141W+N142D+ D143N; Y141W+K192R V410A; G128D+Y141W+

D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 11 for numbering).

In an embodiment the carbohydrate-source generating enzyme and/or the cellulolytic composition are added during pre-saccharification carried out before saccharification step (b) and/or fermentation step (c). The carbohydrate-source generating enzyme and the cellulolytic composition may also be added during pre-saccharification carried out before simultaneous saccharification and fermentation (SSF).

In an embodiment a process of the invention comprises
(a) liquefying a starch containing material with an alpha-amylase;
presaccharifying the liquefied material using a carbohydrate-source generating enzyme and a cellulolytic composition;
(b) saccharifying;
(c) fermenting using a fermentation organism;
wherein saccharification step (b) and fermentation step (c) are carried out simultaneously or sequentially.

In an embodiment a process of the invention comprises
(a) liquefying a starch containing material with an alpha-amylase;
presaccharifying the liquefied material using a carbohydrate-source generating enzyme;
(b) saccharifying in the presence of a cellulolytic composition;
(c) fermenting using a fermentation organism;
wherein saccharification step (b) and fermentation step (c) are carried out simultaneously or sequentially.

In an embodiment the process of the invention the pre-saccharification is carried out at a temperature from 40-75° C., such as 50-70° C., preferably 60° C.; a pH between 4-6, preferably 5; for a period of 30-360 minutes, such as from 60-420 minutes, such as around between 150-180 minutes.

In an embodiment of the invention the carbohydrate-source generating enzyme and/or the cellulolytic composition are added during saccharification step (b) and/or fermentation step (c), or simultaneous saccharification and fermentation (SSF).

In an embodiment the process of the invention comprises
(a) liquefying a starch containing material with an alpha-amylase;
(b) saccharifying the liquefied material in the presence of a carbohydrate-source generating enzyme and a cellulolytic composition;
(c) fermenting using a fermentation organism;
wherein saccharification step (b) and fermentation step (c) are carried out simultaneously or sequentially.

In an embodiment the hemicellulase content in the cellulolytic composition constitutes less than 10 wt. % such as less than 5 wt. % of the cellulolytic composition.

In a preferred embodiment the beta-glucosidase is a variant of the *Aspergillus fumigatus* beta-glucosidase shown in SEQ ID NO: 6 herein, which further comprises one or more substitutions selected from the group consisting of L89M, G91L, F100D, I140V, I186V, S283G, N456E, and F512Y. In a preferred embodiment the *Aspergillus fumigatus* beta-glucosidase is a variant of SEQ ID NO: 6 with any following substitutions:
F100D+S283G+N456E+F512Y;
L89M+G91L+I186V+I140V;
I186V+L89M+G91L+I140V+F100D+S283G+N456E+F512Y (using SEQ ID NO: 6 for numbering).

In a preferred embodiment the cellulolytic composition is derived from *Trichoderma reesei* and further comprising one or more of:
(i) an *Aspergillus fumigatus* cellobiohydrolase I, preferably the one shown in SEQ ID NO: 2 herein;
(ii) an *Aspergillus fumigatus* cellobiohydrolase II, preferably the one shown in SEQ ID NO: 4 herein;
(iii) an *Aspergillus fumigatus* beta-glucosidase variant thereof with the following substitutions: F100D, S283G, N456E, F512Y (using SEQ ID NO: 6 herein for numbering).

In a further embodiment of the process of the invention a trehalase is present or adding during presacharification, saccharification, and/or simultaneous or sequential saccharification and fermentation. As shown in Example 5 combining a cellulolytic composition and a treahalase increases the ethanol yield.

Further, it was also found that processes of the invention result in backend (after recovery of the fermentation product, such as ethanol) benefits. After fermentation the fermentation product may be recovered, preferably by distillation, by separate the fermented material into a liquid fraction (i.e., fermentation product), such as ethanol, and a solid fraction (i.e., whole stillage). After recovery of the fermentation product, the solid fraction (i.e., whole stillage) may be dewatered and separating into a solid phase (i.e., wet cake) and a liquid phase (Thin Stillage), e.g., by centrifugation. As shown in Example 6 improved dewatering is obtained.

In an embodiment the present invention relates to processes of producing fermentation products comprising
(a) liquefying a starch-containing material with an alpha-amylase;
(b) saccharifying the liquefied material using a carbohydrate-source generating enzyme;
(c) fermenting using a fermentation organism in the presence of a cellulolytic composition comprising one or more polypeptides selected from the group consisting of:
  GH61 polypeptide having cellulolytic enhancing activity;
  beta-glucosidase;
  Cellobiohydrolase I;
  Cellobiohydrolase II;
or a mixture of two, three, or four thereof.

In an embodiment the cellulolytic composition is derived from a strain of *Trichoderma reesei*, *Humicola insolens* and/or *Chrysosporium lucknowense*. In an embodiment the cellulolytic composition comprises a beta-glucosidase, a cellobiohydrolase, and an endoglucanase.

In an embodiment the cellulolytic composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in WO 2005/047499 or SEQ ID NO: 6 herein or an *Aspergillus fumigatus* beta-glucosidase variant disclosed in WO 2012/044915 or co-pending PCT application No. PCT/US11/054185 (Novozymes), such as one with the following substitutions F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

In an embodiment the cellulolytic composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of

*Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 8 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 6 in WO 2011/057140 or SEQ ID NO: 2 herein, or a strain of the genus *Trichoderma*, such as a strain of *Trichoderma reesei*.

In an embodiment the cellulolytic composition comprises a cellobiohydrolase II (CBH II, such as one derived from a strain of the genus *Aspergillus*, such as a strain of *Aspergillus fumigatus* or SEQ ID NO: 4 herein; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*. In an embodiment the cellulolytic composition comprises a GH61 polypeptide having cellulolytic enhancing activity and a beta-glucosidase.

In an embodiment the cellulolytic composition comprises beta-glucosidase and a CBH.

In an embodiment the cellulolytic composition comprises a GH61 polypeptide having cellulolytic enhancing activity, a beta-glucosidase, and a CBH I.

In an embodiment the cellulolytic composition comprises a beta-glucosidase and a CBH I.

In an embodiment the cellulolytic composition comprises a GH61 polypeptide having cellulolytic enhancing activity, a beta-glucosidase, a CBH I, and a CBH II.

In an embodiment the cellulolytic composition comprises a beta-glucosidase, a CBH I, and a CBH II.

In a preferred embodiment the beta-glucosidase has a Relative ED50 loading value of less than 1.00, preferably less than 0.80, such as preferably less than 0.60, such as between 0.1-0.9, such as between 0.2-0.8, such as 0.30-0.70. In an embodiment the cellulolytic composition is a *Trichoderma reesei* cellulolytic composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

In an embodiment the cellulolytic composition is a *Trichoderma reesei* cellulolytic composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 6 herein.

In an embodiment the cellulolytic composition is a *Trichoderma reesei* cellulolytic composition further comprising *Penicillium emersonii* GH61A polypeptide having cellulolytic enhancing activity disclosed in WO 2011/041397 and *Aspergillus fumigatus* beta-glucosidase (SEQ ID NO: 2 of WO 2005/047499) or SEQ ID NO: 6 herein or a variant thereof with the following substitutions F100D, S283G, N456E, F512Y.

In a preferred embodiment the invention relates to processes of producing fermentation products, comprising
(a) liquefying a starch-containing material with an alpha-amylase;
(b) saccharifying the liquefied material using a carbohydrate source generating enzyme;
(c) fermenting using a fermentation organism in the presence of a cellulolytic composition comprising one or more of the following components:
(i) an *Aspergillus fumigatus* cellobiohydrolase I preferably the one shown in SEQ ID NO: 2 herein;
(ii) an *Aspergillus fumigatus* cellobiohydrolase II preferably the one shown in SEQ ID NO: 4 herein;
(iii) an *Aspergillus fumigatus* beta-glucosidase preferably the one shown in SEQ ID NO: 6 herein; or variant thereof, such as one with the following substitutions: F100D, S283G, N456E, F512Y (using SEQ ID NO: 6 herein for numbering); and
(iv) a *Penicillium* sp. GH61 polypeptide having cellulolytic enhancing activity preferably the one shown in SEQ ID NO: 8 herein; or homologs thereof.

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Starch is formed within plant cells as tiny granules insoluble in water. When put in cold water, the starch granules may absorb a small amount of the liquid and swell. At temperatures up to about 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. Two processes are preferred according to the invention: wet and dry milling. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

Liquefaction is carried out in the presence of an alpha-amylase, preferably a bacterial alpha-amylase and/or acid fungal alpha-amylase. In an embodiment, a phytase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15.

Generally liquefaction and liquefaction conditions are well known in the art.

Examples of alpha-amylases are disclosed in the "Aplha-Amylases" section below.

Saccharification may be carried out using conditions well known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

In an embodiment of the process of the invention a cellulolytic composition (mentioned in context of the process of the invention) is added during pre-saccharification. In a preferred embodiment the pre-saccharification step is followed by a SSF step. In an embodiment of the invention the cellulolytic composition is added during a pre-saccharification step carried out at temperatures from 40-75° C., such as from 50-70° C., preferably 60° C.; at a pH between 4-6, preferably 5; for a period of 30-360 minutes, such as from 60-420 minutes, such as 150-180 minutes.

The saccharification and fermentation steps may be carried out either sequentially or simultaneously. In an embodiment, saccharification and fermentation are performed simultaneously (referred to as "SSF"). There is no holding stage for the saccharification, meaning that the fermenting organism, such as yeast, and enzyme(s) (is) are added together. SSF is typically carried out at a temperature from 20-40° C., e.g., 26-34° C., preferably around 32° C., when the fermentation organism is yeast, such as a strain of the genus *Saccharomyces*, in particular a strain of *Saccharomyces cerevisiae*, especially when the fermentation product is ethanol.

Other fermentation products may be fermented at conditions and temperatures well known to persons skilled in the art, suitable for the fermenting organism in question.

The fermentation product may be recovered by methods well known in the art, e.g., by distillation. Examples of carbohydrate-source generating enzymes, including glucoamylases, are disclosed in the "Enzymes" section below.

In a particular embodiment, the process of the invention further comprises, prior to the conversion of a starch-containing material to sugars/dextrins the steps of:
(x) reducing the particle size of the starch-containing material; and
(y) forming a slurry comprising the starch-containing material and water.

Methods for reducing the particle size of the starch containing material are well known to those skilled in the art. In an embodiment, the starch-containing material is milled to reduce the particle size.

The aqueous slurry may contain from 10-55 wt. % dry solids (DS), preferably 25-45 wt. % dry solids (DS), more preferably 30-40 wt. % dry solids (DS) of starch-containing material.

In an embodiment the cellulolytic composition and/or carbohydrate-source generating enzyme, such as glucoamylase, are added during pre-saccharification, fermentation, or SSF in accordance with the process of the invention in combination with a protease. This provides an increased ethanol yield. This also provides benefits, e.g., improves oil extraction, at the backend of the process. Specifically contemplated is the combination of a cellulolytic composition comprising one or more of the following components
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof,
and a protease derived from *Thermoascus aurantiacus* CGMCC No. 0670 (classified as EC 3.4.24.39) (disclosed below in the "Protease"-section) and enzymes being at least 60%, such as at least 70%, such as at least 80%, such as at least 90%, such as at least 95%, such as at least 96%, such as at least 97%, as as at least 98%, such as at least 99% identical to SEQ ID NO: 13 herein.

Processes for Producing Fermentation Products from Ungelatinized Starch-Containing Materials The present invention also relates to processes for producing a fermentation product from a starch-containing material without gelatinization (often referred to as "without cooking" or "raw starch hydrolysis" process) of the starch-containing material.

More specifically, in this aspect the invention relates to processes of producing fermentation products, comprising the following steps:
(i) saccharifying a starch-containing material with a carbohydrate-source generating enzymes at a temperature below the initial gelatinization temperature; and
(ii) fermenting using a fermentation organism in the presence of a cellulolytic composition comprising one or more polypeptides selected from the group consisting of:
GH61 polypeptide having cellulolytic enhancing activity;
beta-glucosidase;
Cellobiohydrolase I;
Cellobiohydrolase II;
or a mixture of two, three, or four thereof.

In an embodiment the cellulolytic composition is derived from *Trichoderma reesei, Humicola insolens* or *Chrysosporium lucknowense*.

In an embodiment the cellulolytic composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or SEQ ID NO: 6 herein, or an *Aspergillus fumigatus* beta-glucosidase variant disclosed in WO 2012/044915 or co-pending PCT application PCT/US11/054185 (Novozymes) such as one with the following substitutions: F100D, S283G, N456E, F512Y using SEQ ID NO: 6 herein for numbering; or a strain of the genus *Penicillium*, such as a strain of *Penicillium brasilianum* disclosed in WO 2007/019442, or a strain of the genus *Trichoderma*, such as a strain of *Trichoderma reesei*.

In an embodiment the cellulolytic composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 8 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 2 herein, or a strain of the genus *Trichoderma*, such as a strain of *Trichoderma reesei*.

In an embodiment the cellulolytic composition comprises a cellobiohydrolase II (CBH II, such as one derived from a strain of the genus *Aspergillus*, such as a strain of *Aspergillus fumigatus* or SEQ ID NO: 4 herein; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the cellulolytic composition comprises a beta-glucosidase.

In an embodiment the cellulolytic composition comprises a GH61 polypeptide having cellulolytic enhancing activity and a beta-glucosidase.

In an embodiment the cellulolytic composition comprises a beta-glucosidase and a CBH.

In an embodiment the cellulolytic composition comprises a GH61 polypeptide having cellulolytic enhancing activity, a beta-glucosidase, and a CBH I.

In an embodiment the cellulolytic composition comprises a beta-glucosidase and a CBH I.

In an embodiment the cellulolytic composition comprises a GH61 polypeptide having cellulolytic enhancing activity, a beta-glucosidase, a CBH I, and a CBH II.

In an embodiment the cellulolytic composition comprises a beta-glucosidase, a CBH I, and a CBH II.

In a preferred embodiment the beta-glucosidase has a Relative ED50 loading value of less than 1.00, preferably less than 0.80, such as preferably less than 0.60, such as between 0.1-0.9, such as between 0.2-0.8, such as 0.30-0.70.

In an embodiment the cellulolytic composition is a *Trichoderma reesei* cellulolytic composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

In an embodiment the cellulolytic composition is a *Trichoderma reesei* cellulolytic composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 6 herein.

In an embodiment the cellulolytic composition is a *Trichoderma reesei* cellulolytic composition further comprising *Penicillium emersonii* GH61A polypeptide having cellulolytic enhancing activity disclosed in WO 2011/041397 or SEQ ID NO: 8 herein and *Aspergillus fumigatus* beta-glucosidase (SEQ ID NO: 2 of WO 2005/047499) or SEQ ID NO: 6 herein or a variant with the following substitutions: F100D, S283G, N456E, F512Y.

In an embodiment the cellulolytic composition comprises one or more of the following components
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

In an embodiment cellulolytic composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

In an embodiment the cellulolytic composition is added during fermentation in accordance with the process of the invention in combination with a protease. This provides benefits, e.g., improves oil extraction, done at the backend of the process. Specifically contemplated is the combination of a cellylolytic composition comprising one or more of the following components
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof and a protease derived from *Thermoascus aurantiacus* CGMCC No. 0670 (classified as EC 3.4.24.39) (disclosed below in the "Protease"-section) and enzymes being at least 60%, such as at least 70%, such as at least 80%, such as at least 90%, such as at least 95%, such as at least 96%, such as at least 97%, as as at least 98%, such as at least 99% identical to SEQ ID NO: 13 herein.

Accordingly, this aspect of the invention relates to processes of producing a fermentation product, comprising subjecting a starch-containing material to an alpha-amylase and a carbohydrate-source generating enzyme, in particular a glucoamylase; and fermenting using a fermenting organism in the presence of a cellulolytic enzyme enzymes as described above and as defined in the "Cellulolytic Enzymes" section in a single step and at a temperature below the initial gelatinization temperature of the starch-containing material.

The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled person in the art. Thus, the initial gelatinization temperature may vary according to the plant species, to the particular variety of the plant species as well as with the growth conditions. The initial gelatinization temperature of a given starch-containing material may be determined as the temperature at which birefringence is lost in 5% of the starch granules using the method described by Gorinstein and Lii, 1992, Starch/Starke 44(12): 461-466.

The process of the present invention may further comprise recovering the fermentation product, e.g., by distillation.

The starch-containing material may be a slurry, such as granular starch, having 10-55 wt. % dry solids (DS), preferably 25-45 wt. % dry solids, more preferably 30-40 wt. % dry solids of starch-containing material may be prepared. The slurry may include water and/or process waters, such as stillage (backset), scrubber water, evaporator condensate or distillate, side-stripper water from distillation, or process water from other fermentation product plants. Because the process is carried out below the initial gelatinization temperature and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like.

The starch-containing material may be prepared by reducing the particle size, e.g., by dry or wet milling to 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% of the dry solids in the starch-containing material is converted into a soluble starch hydrolyzate.

The process of this aspect of the invention is conducted at a temperature below the initial gelatinization temperature, e.g., a temperature in the range between 25–40° C., such as 25-40° C., 29-35° C., 30-34° C., such as around 32° C. One skilled in the art can easily determine suitable process conditions.

The process of the invention may be carried out at a pH from about 3 and 7, e.g., 3.5 to 6 or 4 to 5.

In an embodiment fermentation is carried out so that the sugar level, such as glucose level, is kept at a low level, such as below 6 wt. %, below about 3 wt. %, below about 2 wt. %, below about 1 wt. %., below about 0.5 wt. %, below 0.25% wt. %, or below about 0.1 wt. %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt. %, such as below about 0.2 wt. %.

Dewatering Method of the Invention

Fermentation products, such as ethanol, are produced by first degrading starch-containing material into fermentable sugars typically by liquefying and saccharifying the starch-containing material and then converting the fermentable sugars directly or indirectly into the desired fermentation product using a fermenting organism. The fermentation product is then recovered from the fermented material (often referred to as "beer mash"), e.g., by distillation, which separates the desired fermentation product from (other) liquids and/or solids. The remaining faction, referred to as "whole stillage", is dewatered and separated into a solid and a liquid phase, e.g., by centrifugation. The solid phase is referred to as "wet cake" (or "wet grains") and the liquid phase (supernatant) is referred to as "thin stillage". Dewatered wet cake is dried to provide "Distillers Dried Grains" (DDG) used as nutrient in animal feed. Thin stillage is typically evaporated to provide condensate and syrup or may alternatively be recycled directly to the slurry tank as "backset". Condensate may either be forwarded to a methanator before being discharged or may be recycled to the slurry tank. The syrup consisting mainly of limit dextrins and non-fermentable sugars may be blended into DDG or added to the wet cake before drying to produce DDGS (Distillers Dried Grain with Solubles).

According to the invention a process or method of the invention result in improved dewatering. Energy is saved as the drying of the wet cake requires less energy.

Example 6 shows that when carrying out a process of producing a fermentation product of the invention improved dewatering is obtained.

Thus, in an aspect the invention relates to methods of dewatering whole stillage comprising
(a) liquefying a starch-containing material with an alpha-amylase;
optionally pre-saccharifying the liquefied material before step (b);
(b) saccharifying the liquefied material;
(c) fermenting using a fermentation organism;
(d) separating the fermented material into a fermentation product and whole stillage;
(e) dewatering the whole stillage;
wherein a carbohydrate-source generating enzyme and/or a cellulolytic composition is present or added during the optional presaccharification step, saccharification step (b), and/or fermentation step (c), or simultaneous saccharification and fermentation.

The cellulolytic composition is preferably adding in from 1-500, such as 10-400, such as 25-300, such as 50-200 micro g/g DS.

In an embodiment the fermentation product is recovered from the fermented material by distillation.

In an embodiment a protease, such as one derived from *Thermoascus aurantiacus*, or a proteases being at least 60%, such as at least 70%, such as at least 80%, such as at least 90%, such as at least 95%, such as at least 96%, such as at least 97%, as as at least 98%, such as at least 99% identical to SEQ ID NO: 13 herein, is added together with the carbohydrate source generating enzymes and cellulolytic composition.

Further, it is also contemplated to add the cellulolytic composition directly to the whole stillage to obtain improved dewatering. Therefore, in one aspect, the invention relates to methods of dewatering whole stillage comprising the steps of:
i) subjecting whole stillage to a cellulolytic composition defined in accordance with the present process of the invention,
ii) separating the material into a solid fraction and a liquid fraction.

The contemplated enzymes used are as disclosed in connection with the process of producing a fermentation product of the invention and in the "Enzymes"-section below.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In a preferred embodiment the fermentation product is ethanol.

Fermenting Organisms

The term "fermenting organism" refers to any organism, including bacterial and fungal organisms, such as yeast and filamentous fungi, suitable for producing a desired fermentation product. Suitable fermenting organisms according to the invention are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans, Candida boidinii, Candida diddensii, Candida shehatae, Candida sonorensis, Candida tropicalis*, or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes*, and strains of *Thermoanaerobacter*, in particular *Thermoanaerobacter* BG1L1 (*Appl. Microbiol. Biotech.* 77: 61-86), *Thermoanarobacter ethanolicus, Thermoanaerobacter mathranii*, or *Thermoanaerobacter thermosaccharolyticum*. Strains of *Lactobacillus* are also envisioned as are strains of *Corynebacterium glutamicum* R, *Bacillus thermoglucosidaisus*, and *Geobacillus thermoglucosidasius*.

In an embodiment the fermenting organism is a C6 sugar fermenting organism, such as a strain of, e.g., *Saccharomyces cerevisiae*.

In an embodiment the fermenting organism is a C5 sugar fermenting organism, such as a strain of, e.g., *Saccharomyces cerevisiae*.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

In an embodiment the C5 utilizing yeast is a *Saccharomyces cerevisea* strain disclosed in WO 2004/085627.

In an embodiment the fermenting organism is a C5 eukaryotic microbial cell concerned in WO 2010/074577 (Nedalco).

In an embodiment the fermenting organism is a transformed C5 eukaryotic cell capable of directly isomerize xylose to xylose disclosed in US 2008/0014620.

In an embodiment the fermenting organism is a C5 sugar fermentating cell disclosed in WO 2009/109633.

Commercially available yeast include LNF SA-1, LNF BG-1, LNF PE-2, and LNF CAT-1 (available from LNF Brazil), RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

According to the invention the fermenting organism capable of producing a desired fermentation product from fermentable sugars is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may according to the invention be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Other fermentation products may be fermented at temperatures known to the skilled person in the art to be suitable for the fermenting organism in question.

Fermentation is typically carried out at a pH in the range between 3 and 7, preferably from pH 3.5 to 6, such as around pH 5. Fermentations are typically ongoing for 6-96 hours.

The processes of the invention may be performed as a batch or as a continuous process. Fermentations may be conducted in an ultrafiltration system wherein the retentate is held under recirculation in the presence of solids, water, and the fermenting organism, and wherein the permeate is the desired fermentation product containing liquid. Equally contemplated are methods/processes conducted in continuous membrane reactors with ultrafiltration membranes and where the retentate is held under recirculation in presence of solids, water, and the fermenting organism(s) and where the permeate is the fermentation product containing liquid.

After fermentation the fermenting organism may be separated from the fermented slurry and recycled.

Fermentation Medium

The phrase "fermentation media" or "fermentation medium" refers to the environment in which fermentation is carried out and comprises the fermentation substrate, that is, the carbohydrate source that is metabolized by the fermenting organism(s).

The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof.

Recovery

Subsequent to fermentation, the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

Enzymes

The enzyme(s) and polypeptides described below are to be used in an "effective amount" in processes of the present invention. Below should be read in context of the enzyme disclosure in the "Definitions"-section above.

Cellulolytic Compositions Used in a Process and Method of the Invention

The cellulolytic composition used in a process of the invention for producing fermentation products may be derived from any microorganism.

In an embodiment the cellulolytic composition is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*.

In a preferred embodiment the cellulolytic composition is derived from a strain of *Trichoderma reesei*.

The cellulolytic composition may comprise one or more of the following polypeptides, including enzymes: GH61 polypeptide having cellulolytic enhancing activity, beta-glucosidase, CBHI and CBHII, or a mixture of two, three, or four thereof.

In a preferred embodiment the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

The cellulolytic composition may comprise some hemicellulase, such as, e.g., xylanase and/or beta-xylosidase. The hemicellulase may come from the cellulolytic composition producing organism or from other sources, e.g., the hemicellulase may be foreign to the cellulolytic composition producing organism, such as, e.g., *Trichoderma reesei*.

In a preferred embodiment the hemicellulase content in the cellulolytic composition constitutes less than 10 wt. % such as less than 5 wt. % of the cellulolytic composition.

In an embodiment the cellulolytic composition comprises a beta-glucosidase.

In an embodiment the cellulolytic composition comprises a GH61 polypeptide having cellulolytic enhancing activity and a beta-glucosidase.

In another embodiment the cellulolytic composition comprises a beta-glucosidase and a CBH.

In another embodiment the cellulolytic composition comprises a GH61 polypeptide having cellulolytic enhancing activity, a beta-glucosidase, and a CBHI.

In another embodiment the cellulolytic composition comprises a beta-glucosidase and a CBHI.

In another embodiment the cellulolytic composition comprises a GH61 polypeptide having cellulolytic enhancing activity, a beta-glucosidase, a CBHI, and a CBHII.

In another embodiment the cellulolytic composition comprises a beta-glucosidase, a CBHI, and a CBHII.

The cellulolytic composition may further comprise one or more enzymes selected from the group consisting of a cellulase, a GH61 polypeptide having cellulolytic enhancing activity, an esterase, an expansin, a laccase, a ligninolytic enzyme, a pectinase, a peroxidase, a protease, and a swollenin.

In an embodiment the cellulase is one or more enzymes selected from the group consisting of an endoglucanase, a cellobiohydrolase, and a beta-glucosidase.

In an embodiment the endoglucanase is an endoglucanase I.

In an embodiment the endoglucanase is an endoglucanase II.

Beta-Glucosidase

The cellulolytic composition used according to the invention may in one embodiment comprise one or more beta-glucosidase. The beta-glucosidase may in one embodiment be one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or SEQ ID NO: 6 herein or an *Aspergillus fumigatus* beta-glucosidase variant, such as one disclosed in WO 2012/044915 or co-pending PCT application PCT/US11/054185 (or U.S. provisional application No. 61/388,997), such as one with the following substitutions: F100D, S283G, N456E, F512Y.

In another embodiment the beta-glucosidase is derived from a strain of the genus *Penicillium*, such as a strain of the *Penicillium brasilianum* disclosed in WO 2007/019442, or a strain of the genus *Trichoderma*, such as a strain of *Trichoderma reesei*.

In an embodiment betaglucosidase is an *Aspergillus fumigatus* beta-glucosidase or homolog thereof selected from the group consisting of:

(i) a beta-glucosidase comprising the mature polypeptide of SEQ ID NO: 6;

(ii) a beta-glucosidase comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 6 herein;
(iii) a beta-glucosidase encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 5 herein; and
(iv) a beta-glucosidase encoded by a polynucleotide that hybridizes under at least high stringency conditions, e.g., very high stringency conditions, with the mature polypeptide coding sequence of SEQ ID NO: 5 herein or the full-length complement thereof.

In an embodiment the beta-glucosidase is a variant comprises a substitution at one or more (several) positions corresponding to positions 100, 283, 456, and 512 of the mature polypeptide of SEQ ID NO: 6 herein, wherein the variant has beta-glucosidase activity.

In an embodiment the parent beta-glucosidase of the variant is (a) a polypeptide comprising the mature polypeptide of SEQ ID NO: 6 herein; (b) a polypeptide having at least 80% sequence identity to the mature polypeptide of SEQ ID NO: 6 herein; (c) a polypeptide encoded by a polynucleotide that hybridizes under high or very high stringency conditions with (i) the mature polypeptide coding sequence of SEQ ID NO: 5 herein, (ii) the cDNA sequence contained in the mature polypeptide coding sequence of SEQ ID NO: 5 herein, or (iii) the full-length complementary strand of (i) or (ii); (d) a polypeptide encoded by a polynucleotide having at least 80% identity to the mature polypeptide coding sequence of SEQ ID NO: 5 herein or the cDNA sequence thereof; or (e) a fragment of the mature polypeptide of SEQ ID NO: 6 herein, which has beta-glucosidase activity.

In an embodiment the beta-glucosidase variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

In an embodiment the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 6 herein.

In an embodiment the beta-glucosidase is from a strain of Aspergillus, such as a strain of Aspergillus fumigatus, such as Aspergillus fumigatus beta-glucosidase (SEQ ID NO: 6 herein), which comprises one or more substitutions selected from the group consisting of L89M, G91L, F100D, I140V, I186V, S283G, N456E, and F512Y; such as a variant thereof with the following substitutions:

F100D+S283G+N456E+F512Y;
L89M+G91L+I186V+I140V;
I186V+L89M+G91L+I140V+F100D+S283G+N456E+F512Y.

In an embodiment the number of substitutions is between 1 and 4, such as 1, 2, 3, or 4 substitutions.

In an embodiment the variant comprises a substitution at a position corresponding to position 100, a substitution at a position corresponding to position 283, a substitution at a position corresponding to position 456, and/or a substitution at a position corresponding to position 512.

In a preferred embodiment the beta-glucosidase variant comprises the following substitutions: Phe100Asp, Ser283Gly, Asn456Glu, Phe512Tyr in SEQ ID NO: 6 herein.

In a preferred embodiment the beta-glucosidase has a Relative ED50 loading value of less than 1.00, preferably less than 0.80, such as preferably less than 0.60, such as between 0.1-0.9, such as between 0.2-0.8, such as 0.30-0.70.

GH61 Polypeptide Having Cellulolytic Enhancing Activity

The cellulolytic composition used according to the invention may in one embodiment comprise one or more GH61 polypeptide having cellulolytic enhancing activity. In one embodiment the enzyme composition comprises a GH61 polypeptide having cellulolytic enhancing activity, such as one derived from the genus Thermoascus, such as a strain of Thermoascus aurantiacus, such as the one described in WO 2005/074656 as SEQ ID NO: 2; or one derived from the genus Thielavia, such as a strain of Thielavia terrestris, such as the one described in WO 2005/074647 as SEQ ID NO: 7 and SEQ ID NO: 8; or one derived from a strain of Aspergillus, such as a strain of Aspergillus fumigatus, such as the one described in WO 2010/138754 as SEQ ID NO: 2; or one derived from a strain derived from Penicillium, such as a strain of Penicillium emersonii, such as the one disclosed in WO 2011/041397 or SEQ ID NO: 8 herein In an embodiment the Penicillium sp. GH61 polypeptide having cellulolytic enhancing activity or homolog thereof is selected from the group consisting of:
(i) a GH61 polypeptide having cellulolytic enhancing activity comprising the mature polypeptide of SEQ ID NO: 8 herein;
(ii) a GH61 polypeptide having cellulolytic enhancing activity comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 8 herein;
(iii) a GH61 polypeptide having cellulolytic enhancing activity encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 7 herein; and
(iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 herein or the full-length complement thereof.

Cellobiohydrolase I

The cellulolytic composition used according to the invention may in one embodiment may comprise one or more CBH I (cellobiohydrolase I). In one embodiment the cellulolytic composition comprises a cellobiohydrolase I (CBHI), such as one derived from a strain of the genus Aspergillus, such as a strain of Aspergillus fumigatus, such as the Cel7A CBHI disclosed in SEQ ID NO: 6 in WO 2011/057140 or SEQ ID NO: 2 herein, or a strain of the genus Trichoderma, such as a strain of Trichoderma reesei.

In an embodiment the Aspergillus fumigatus cellobiohydrolase I or homolog thereof is selected from the group consisting of:
(i) a cellobiohydrolase I comprising the mature polypeptide of SEQ ID NO: 2 herein;
(ii) a cellobiohydrolase I comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 2 herein;
(iii) a cellobiohydrolase I encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 1 herein; and (iv) a cellobiohydrolase I encoded by a polynucleotide that hybridizes under at least high stringency conditions, e.g., very high stringency conditions, with the mature polypeptide coding sequence of SEQ ID NO: 1 herein or the full-length complement thereof.

Cellobiohydrolase II

The cellulolytic composition used according to the invention may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*, such as the one in SEQ ID NO: 4 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the *Aspergillus fumigatus* cellobiohydrolase II or homolog thereof is selected from the group consisting of:

(i) a cellobiohydrolase II comprising the mature polypeptide of SEQ ID NO: 4 herein;

(ii) a cellobiohydrolase II comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 4 herein;

(iii) a cellobiohydrolase II encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 3 herein; and (iv) a cellobiohydrolase II encoded by a polynucleotide that hybridizes under at least high stringency conditions, e.g., very high stringency conditions, with the mature polypeptide coding sequence of SEQ ID NO: 3 herein or the full-length complement thereof.

Cellulolytic Compositions

As mentioned above the cellulolytic composition may comprise a number of difference polypeptides, such as enzymes.

In an embodiment the cellulolytic composition comprises a *Trichoderma reesei* cellulolytic composition, further comprising *Thermoascus aurantiacus* GH61A polypeptide having cellulolytic enhancing activity (WO 2005/074656) and *Aspergillus oryzae* beta-glucosidase fusion protein (WO 2008/057637).

In another embodiment the cellulolytic composition comprises a *Trichoderma reesei* cellulolytic composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499).

In another embodiment the cellulolytic composition comprises a *Trichoderma reesei* cellulolytic composition, further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) or a variant thereof with the following substitutions: F100D, S283G, N456E, F512Y.

The enzyme composition of the present invention may be in any form suitable for use, such as, for example, a crude fermentation broth with or without cells removed, a cell lysate with or without cellular debris, a semi-purified or purified enzyme composition, or a host cell, e.g., *Trichoderma* host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In an preferred embodiment the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

Alpha-Amylases

According to the invention any alpha-amylase may be used, such as of fungal, bacterial or plant origin. In a preferred embodiment the alpha-amylase is an acid alpha-amylase, e.g., acid fungal or acid bacterial alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

An alpha-amylase for use in the present invention may be a bacterial alpha-amylase, e.g., derived from *Bacillus*. In a preferred embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of alpha-amylases include the *Bacillus amyloliquefaciens* alpha-amylase of SEQ ID NO: 5 in WO 99/19467, the *Bacillus licheniformis* alpha-amylase of SEQ ID NO: 4 in WO 99/19467, and the *Bacillus stearothermophilus* alpha-amylase of SEQ ID NO: 3 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, and 6,297,038 (hereby incorporated by reference) and include *Bacillus stearothermophilus* alpha-amylase (BSG alpha-amylase) variants having a deletion of one or two amino acids at positions R179 to G182, preferably a double deletion disclosed in WO 96/23873—see, e.g., page 20, lines 1-10 (hereby incorporated by reference), preferably corresponding to delta (181-182) compared to the amino acid sequence of *Bacillus stearothermophilus* alpha-amylase set forth in SEQ ID NO: 3 disclosed in WO 99/19467 or the deletion of amino acids R179 and G180 using SEQ ID NO: 3 in WO 99/19467 for numbering (which reference is hereby incorporated by reference). Even more preferred are *Bacillus* alpha-amylases, especially *Bacillus stearothermophilus* alpha-amylases, which have a double deletion corresponding to delta (181-182) and further comprise a N193F substitution (also denoted I181*+G182*+N193F) compared to the wild-type BSG alpha-amylase amino acid sequence set forth in SEQ ID NO: 3 disclosed in WO 99/19467.

Bacterial Hybrid Alpha-Amylases

The alpha-amylase may be a hybrid alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with one or more, especially all, of the following substitutions:
G48A+T49I+G107A+H156Y+A181T+N190F+I201F+ A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment, the bacterial alpha-amylase is dosed in an amount of 0.0005-5 KNU per g DS (dry solids), preferably 0.001-1 KNU per g DS, such as around 0.050 KNU per g DS.

Fungal Alpha-Amylases

Fungal alpha-amylases include alpha-amylases derived from a strain of *Aspergillus*, such as, *Aspergillus kawachii*, *Aspergillus niger* and *Aspergillus oryzae* alpha-amylases.

A preferred acidic fungal alpha-amylase is an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain of *Aspergillus niger*. In a preferred embodiment the acid fungal alpha-amylase is an *Aspergillus niger* alpha-amylase disclosed as "AMYA_ASPNG" in the Swiss-prot/TeEMBL database under the primary accession no. P56271 and described in WO 89/01969 (Example 3—incorporated by reference). A commercially available acid fungal alpha-amylase derived from *Aspergillus niger* is SP288 (available from Novozymes A/S, Denmark).

Other wild-type alpha-amylases include those derived from a strain of *Meripilus* and *Rhizomucor*, preferably a strain of *Meripilus giganteus* or *Rhizomucor pusillus* (WO 2004/055178 which is incorporated herein by reference).

In a preferred embodiment the alpha-amylase is derived from *Aspergillus kawachii* (Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL: #AB008370).

The fungal alpha-amylase may also be a wild-type enzyme comprising a starch-binding domain (SBD) and an alpha-amylase catalytic domain, or a variant thereof.

Fungal Hybrid Alpha-Amylases

In a preferred embodiment the fungal acid alpha-amylase is a hybrid alpha-amylase. Examples of fungal hybrid alpha-amylases include the ones disclosed in WO 2005/003311, U.S. Patent Application Publication No. 2005/0054071 (Novozymes), and WO 2006/069290 (Novozymes), which are hereby incorporated by reference. A hybrid alpha-amylase may comprise an alpha-amylase catalytic domain (CD) and a carbohydrate-binding domain/module (CBM), such as a starch binding domain (SBD), and optionally a linker.

Examples of hybrid alpha-amylases include those disclosed in Tables 1 to 5 of the examples in WO 2006/069290 including the variant with the catalytic domain JA118 and *Athelia rolfsii* SBD (SEQ ID NO: 100 in WO 2006/069290), *Rhizomucor pusillus* alpha-amylase with *Athelia rolfsii* AMG linker and SBD (SEQ ID NO: 101 in WO 2006/069290), *Rhizomucor pusillus* alpha-amylase with *Aspergillus niger* glucoamylase linker and SBD (which is disclosed in Table 5 as a combination of amino acid sequences SEQ ID NO: 20, SEQ ID NO: 72 and SEQ ID NO: 96 in U.S. application Ser. No. 11/316,535) or as V039 in Table 5 in WO 2006/069290 and SEQ ID NO: 11 herein, and *Meripilus giganteus* alpha-amylase with *Athelia rolfsii* glucoamylase linker and SBD (SEQ ID NO: 102 in WO 2006/069290). Other hybrid alpha-amylases are listed in Tables 3, 4, 5, and 6 in Example 4 in U.S. application Ser. No. 11/316,535 and WO 2006/069290 (which are hereby incorporated by reference).

In a preferred embodiment the alpha-amylase is a *Rhizomucor pusillus* alpha-amylase. In an embodiment the alpha-amylase is a hybrid further comprising a linker and a carbohydrate binding module. In an embodiment the *Rhizomucor pusillus* alpha-amylase has *Aspergillus niger* glucoamylase linker and SBD disclosed as V039 in Table 5 in WO 2006/069290 or SEQ ID NO: 11 herein. Specifically contemplated are *Rhizomucor pusillus* alpha-amylase variants disclosed in WO2013/006756 (hereby incorporated by reference)

The *Rhizomucor pusillus* alpha-amylase variant may be one comprising a substitution at one or more positions corresponding to positions 128, 143, 141, 192, 20, 76, 123, 136, 142, 165, 219, 224, 265, 383, and 410 of the mature polypeptide of SEQ ID NO: 11, wherein the variant has alpha amylase activity.

In an embodiment the variant alpha amylase has at least 60%, e.g., at least 65%, at least 70%, at least 75%, at least 80%, at least 85%, at least 90%, at least 95%, at least 96%, at least 97%, at least 98%, or at least 99%, but less that 100% sequence identity with the mature polypeptide of SEQ ID NO: 11.

In an embodiment the parent alpha-amylase has at least 60%, e.g., at least 65%, at least 70%, at least 75%, at least 80%, at least 85%, at least 90%, at least 95%, at least 96%, at least 97%, at least 98%, and/or at least 99% sequence identity with the mature polypeptide of SEQ ID NO: 11.

In preferred embodiments the alpha-amylase variant comprises at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219Q+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 11 for numbering).

Other examples of hybrid alpha-amylases include those disclosed in U.S. Patent Application Publication No. 2005/0054071, including those disclosed in Table 3 on page 15, such as *Aspergillus niger* alpha-amylase with *Aspergillus kawachii* linker and starch binding domain.

Other alpha-amylases exhibit a high degree of sequence identity to any of above mentioned alpha-amylases, i.e., at least 70%, at least 75%, at least 80%, at least 85%, at least 90%, at least 95%, at least 96%, at least 97%, at least 98%, at least 99% or even 100% identity to the mature enzyme sequences disclosed above.

An acid alpha-amylase may according to the invention be added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

Commercial Alpha-Amylase Products

Preferred commercial compositions comprising alpha-amylase include MYCOLASE™ (DSM), BAN™, TERMAMYL™ SC, FUNGAMYL™, LIQUOZYME™ X, LIQUOZYME™ SC and SAN™ SUPER, SAN™ EXTRA L (Novozymes A/S) and CLARASE™ L-40,000, DEXLO™, SPEZYME™ FRED, SPEZYME™ AA, SPEZYME™ ALPHA, SPEZYME™ DELTA AA, GC358, GC980, SPEZYME™ CL and SPEZYME™ RSL (Danisco A/S), and the acid fungal alpha-amylase from *Aspergillus niger* referred to as SP288 (available from Novozymes A/S, Denmark).

Carbohydrate-Source Generating Enzymes (Saccharifying Enzymes)

The term "carbohydrate-source generating enzyme" includes glucoamylase (a glucose generator), beta-amylase and maltogenic amylase (both maltose generators) and also alpha-glucosidase, isoamylase and pullulanase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Blends include mixtures comprising at least a glucoamylase and an alpha-amylase, especially an acid amylase, even more preferred an acid fungal alpha-amylase.

The ratio between glucoamylase activity (AGU) and acid fungal alpha-amylase activity (FAU-F) (i.e., AGU per FAU-F) may in a preferred embodiment of the invention be between 0.1 and 100 AGU/FAU-F, in particular between 2 and 50 AGU/FAU-F, such as in the range from 10-40 AGU/FAU-F, especially when performing a one-step fermentation (raw starch hydrolysis—RSH), i.e., when saccharification and fermentation are carried out simultaneously (i.e., without a liquefaction step).

In a conventional starch-to-ethanol process (i.e., including a liquefaction step) the ratio may preferably be as defined in EP 140410, especially when saccharification and fermentation are carried out simultaneously.

Glucoamylases

A glucoamylase may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Hata et al., 1991, *Agric. Biol. Chem.* 55(4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, Biochem. J. 301: 275-281); disulphide bonds, A246C (Fierobe et al., 1996, *Biochemistry* 35: 8698-8704; and introduction of Pro residues in positions A435 and S436 (Li et al., 1997, *Protein Eng.* 10: 1199-1204.

Other glucoamylases include *Athelia rolfsii* (previously denoted *Corticium rolfsii*) glucoamylase (see U.S. Pat. No. 4,727,026 and Nagasaka et al., 1998, *Appl. Microbiol. Biotechnol.* 50: 323-330), *Talaromyces* glucoamylases, in particular derived from *Talaromyces duponti, Talaromyces emersonii* (WO 99/28448), *Talaromyces leycettanus* (U.S. Pat. No. Re. 32,153), and *Talaromyces thermophilus* (U.S. Pat. No. 4,587,215).

Bacterial glucoamylases include glucoamylases from *Clostridium*, in particular *C. thermoamylolyticum* (EP 135138) and *C. thermohydrosulfuricum* (WO 86/01831), *Trametes cingulata, Pachykytospora papyracea*, and *Leucopaxillus giganteus*, all disclosed in WO 2006/069289; or *Peniophora rufomarginata* disclosed in WO2007/124285 or PCT/US2007/066618; or a mixture thereof. A hybrid glucoamylase may be used in the present invention. Examples of hybrid glucoamylases are disclosed in WO 2005/045018. Specific examples include the hybrid glucoamylase disclosed in Tables 1 and 4 of Example 1 (which hybrids are hereby incorporated by reference).

The glucoamylase may have a high degree of sequence identity to any of above mentioned glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Commercially available glucoamylase compositions include AMG 200L; AMG 300L; SAN™ SUPER, SAN™ EXTRA L, SPIRIZYME™ PLUS, SPIRIZYME™ FUEL, SPIRIZYME™ B4U, SPIRIZYME ULTRA, SPIRIZYME™ EXCEL and AMG™ E (from Novozymes A/S, Denmark); OPTIDEX™ 300, GC480™ and GC147™ (from Genencor Int., USA); AMIGASE™ and AMIGASE™ PLUS (from DSM); G-ZYME™ G900, G-ZYME™ and G990 ZR (from Genencor Int.).

Glucoamylases may be added in an amount of 0.02-20 AGU/g DS, preferably 0.1-10 AGU/g DS, especially between 1-5 AGU/g DS, such as 0.1-2 AGU/g DS, such as 0.5 AGU/g DS or in an amount of 0.0001-20 AGU/g DS, preferably 0.001-10 AGU/g DS, especially between 0.01-5 AGU/g DS, such as 0.1-2 AGU/g DS.

Beta-Amylases

A beta-amylase (E.C. 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (Fogarty and Kelly, 1979, *Progress in Industrial Microbiology* 15: 112-115). These beta-amylases are characterized by having a temperature optimum in the range from 40° C. to 65° C. and a pH optimum in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylases

The amylase may also be a maltogenic alpha-amylase (glucan 1,4-alpha-maltohydrolase, EC 3.2.1.133), which catalyzes the hydrolysis of amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may be added in an amount of 0.05-5 mg total protein/gram DS or 0.05-5 MANU/g DS.

Phytases

Any phytase may be used in a process of the present invention. Phytases are enzymes that degrade phytates and/or phytic acid by specifically hydrolyzing the ester link between inositol and phosphorus. Phytase activity is credited with phosphorus and ion availability in many ingredients. In some embodiments, the phytase is capable of liberating at least one inorganic phosphate from an inositol hexaphosphate (e.g., phytic acid). Phytases can be grouped according to their preference for a specific position of the phosphate ester group on the phytate molecule at which hydrolysis is initiated (e.g., 3-phytase (EC 3.1.3.8) or 6-phytase (EC 3.1.3.26)). An example of phytase is myo-inositol-hexakiphosphate-3-phosphohydrolase.

Phytases can be obtained from microorganisms such as fungal and bacterial organisms. For example, the phytase may be obtained from filamentous fungi such as *Aspergillus* (e.g., *A. ficuum, A. fumigatus, A. niger,* and *A. terreus*), *Cladospirum, Mucor* (e.g., *Mucor piriformis*), *Myceliophthora* (e.g., *M. thermophila*), *Penicillium* (e.g., *P. hordei* (ATCC No. 22053)), *P. piceum* (ATCC No. 10519), or *P. brevi-compactum* (ATCC No. 48944), *Talaromyces* (e.g., *T. thermophilus*), *Thermomyces* (WO 99/49740), and *Trichoderma* spp. (e.g., *T. reesei*).

In an embodiment, the phytate-degrading enzyme is obtained from yeast (e.g., *Arxula adeninivorans, Pichia anomala, Schwanniomyces occidentalis*), gram-negative bacteria (e.g., *Escherichia coli, Klebsiella* spp., *Pseudomonas* spp.), and gram-positive bacteria (e.g., *Bacillus* spp. such as *Bacillus subtilis*).

The phytase also may be obtained from *Citrobacter, Enterbacter,* or *Peniophora.*

In an embodiment, the phytase is derived from *Buttiauxiella* spp. such as *B. agrestis, B. brennerae, B. ferragutiase, B. gaviniae, B. izardii, B. noackiae,* and *B. warmboldiae.* In some embodiments, the phytase is a phytase disclosed in WO 2006/043178 or U.S. application Ser. No. 11/714,487.

In one preferred embodiment, the phytase has at least 75%, at least 80%, at least 85%, at least 88%, at least 90%, at least 93%, at least 95%, at least 96%, at least 97%, at least 98% and at least 99% sequence identity to the amino acid sequence set forth in SEQ ID NO: 31 of U.S. application Ser. No. 12/263,886.

Commercially-available phytases are NATUPHOS (BASF), RONOZYME P (Novozymes A/S), PHZYME (Danisco A/S, Diversa) and FINASE (AB Enzymes). The method for determining microbial phytase activity and the definition of a phytase unit is disclosed in Engelen et al., 1994, *Journal of AOAC International* 77: 760-764. The phytase may be a wild-type phytase, an active variant or active fragment thereof.

Pullulanases

Any pullulanase may be used in a process of the present invention. In an embodiment, the pullulanase is a GH57 pullulanase, e.g., a pullulanase obtained from a strain of *Thermococcus*, including *Thermococcus* sp. AM4, *Thermococcus* sp. HJ21, *Thermococcus barophilus, Thermococcus gammatolerans, Thermococcus hydrothermalis, Thermococcus kodakarensis, Thermococcus litoralis,* and *Thermococcus onnurineus*; or from a strain of *Pyrococcus*, such as *Pyrococcus abyssi* and *Pyrococcus furiosus.*

Proteases

A protease may be added during pre-saccharification, saccharification, fermentation, simultaneous saccharification and fermentation in above concerned processes including a liquefaction step (i.e., where the starch-containing material is gelatinized). A protease may also be added during fermentation in above concerned raw starch processes (i.e., where the starch-containing material is ungelatinized). The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

The acid fungal protease may be derived from *Aspergillus, Candida, Coriolus, Endothia, Enthomophtra, Irpex, Mucor, Penicillium, Rhizopus, Sclerotium,* and *Torulopsis.* In particular, the protease may be derived from *Aspergillus aculeatus* (WO 95/02044), *Aspergillus awamori* (Hayashida et al., 1977, *Agric. Biol. Chem.* 42(5), 927-933), *Aspergillus niger* (see, e.g., Koaze et al., 1964, *Agr. Biol. Chem.* Japan 28: 216), *Aspergillus saitoi* (see, e.g., Yoshida, 1954, *J. Agr. Chem. Soc.* Japan 28: 66), or *Aspergillus oryzae*, such as the pepA protease; and acidic proteases from *Mucor miehei* or *Mucor pusillus.*

The protease may be a neutral or alkaline protease, such as a protease derived from a strain of *Bacillus*. A particular protease is derived from *Bacillus amyloliquefaciens* and has the sequence obtainable at Swissprot as Accession No. P06832. The proteases may have at least 90% sequence identity to the amino acid sequence disclosed in the Swissprot Database, Accession No. P06832 such as at least 92%, at least 95%, at least 96%, at least 97%, at least 98%, or particularly at least 99% identity.

The protease may have at least 60%, such as at least 70%, such as at least 80%, such as at least 90% sequence identity to the amino acid sequence disclosed as SEQ ID NO: 1 in WO 2003/048353 or SEQ ID NO: 13 herein such as at 92%, at least 95%, at least 96%, at least 97%, at least 98%, or particularly at least 99% identity.

The protease may be a papain-like protease selected from the group consisting of proteases within EC 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

In an embodiment, the protease is a protease preparation derived from a strain of *Aspergillus*, such as *Aspergillus oryzae*. In another embodiment the protease is derived from a strain of *Rhizomucor*, preferably *Rhizomucor miehei*. In another embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor miehei.*

Aspartic acid proteases are described in, for example, Handbook of Proteolytic Enzymes, Edited by A. J. Barrett, N. D. Rawlings and J. F. Woessner, Academic Press, San Diego, 1998, Chapter 270. Examples of aspartic acid proteases include, e.g., those disclosed in Berka et al., 1990, Gene 96: 313; Berka et al., 1993, *Gene* 125: 195-198; and Gomi et al., 1993, *Biosci. Biotech. Biochem.* 57: 1095-1100, which are hereby incorporated by reference.

The protease also may be a metalloprotease, which is defined as a protease selected from the group consisting of: (a) proteases belonging to EC 3.4.24 (metalloendopeptidases); preferably EC 3.4.24.39 (acid metallo proteinases); (b) metalloproteases belonging to the M group of the above Handbook;

(c) metalloproteases not yet assigned to clans (designation: Clan MX), or belonging to either one of clans MA, MB, MC, MD, ME, MF, MG, MH (as defined at pp. 989-991 of the above Handbook);
(d) other families of metalloproteases (as defined at pp. 1448-1452 of the above Handbook);
(e) metalloproteases with a HEXXH motif;
(f) metalloproteases with an HEFTH motif;
(g) metalloproteases belonging to either one of families M3, M26, M27, M32, M34, M35, M36, M41, M43, or M47 (as defined at pp. 1448-1452 of the above Handbook);
(h) metalloproteases belonging to the M28E family; and
(i) metalloproteases belonging to family M35 (as defined at pp. 1492-1495 of the above Handbook).

In other particular embodiments, metalloproteases are hydrolases in which the nucleophilic attack on a peptide bond is mediated by a water molecule, which is activated by a divalent metal cation. Examples of divalent cations are zinc, cobalt or manganese. The metal ion may be held in place by amino acid ligands. The number of ligands may be five, four, three, two, one or zero. In a particular embodiment the number is two or three, preferably three.

There are no limitations on the origin of the metalloprotease used in a process of the invention. In an embodiment the metalloprotease is classified as EC 3.4.24, preferably EC 3.4.24.39. In one embodiment, the metalloprotease is an acid-stable metalloprotease, e.g., a fungal acid-stable metalloprotease, such as a metalloprotease derived from a strain of the genus Thermoascus, preferably a strain of Thermoascus aurantiacus, especially Thermoascus aurantiacus CGMCC No. 0670 (classified as EC 3.4.24.39). In another embodiment, the metalloprotease is derived from a strain of the genus Aspergillus, preferably a strain of Aspergillus oryzae.

In one embodiment the metalloprotease has a degree of sequence identity to amino acids −178 to 177, −159 to 177, or preferably amino acids 1 to 177 (the mature polypeptide) of SEQ ID NO: 1 of WO 2010/008841 or SEQ ID NO: 13 herein (a Thermoascus aurantiacus metalloprotease) of at least 60%, such as at least 70%, such as at least 80%, at least 82%, at least 85%, at least 90%, at least 95%, at least 97%, such as 99%; and which have metalloprotease activity. In particular embodiments, the metalloprotease consists of an amino acid sequence with a degree of identity to SEQ ID NO: 1 or SEQ ID NO: 13 herein as mentioned above.

The Thermoascus aurantiacus metalloprotease is a preferred example of a metalloprotease suitable for use in a process of the invention. Another metalloprotease is derived from Aspergillus oryzae and comprises the sequence of SEQ ID NO: 11 disclosed in WO 2003/048353, or amino acids −23-353; −23-374; −23-397; 1-353; 1-374; 1-397; 177-353; 177-374; or 177-397 thereof, and SEQ ID NO: 10 disclosed in WO 2003/048353.

Another metalloprotease suitable for use in a process of the invention is the Aspergillus oryzae metalloprotease comprising SEQ ID NO: 5 of WO 2010/008841, or a metalloprotease is an isolated polypeptide which has a degree of identity to SEQ ID NO: 5 of at least about 80%, at least 82%, at least 85%, at least 90%, at least 95%, or at least 97%; and which have metalloprotease activity. In particular embodiments, the metalloprotease consists of the amino acid sequence of SEQ ID NO: 5.

In a particular embodiment, a metalloprotease has an amino acid sequence that differs by forty, thirty-five, thirty, twenty-five, twenty, or by fifteen amino acids from amino acids −178 to 177, −159 to 177, or +1 to 177 of the amino acid sequences of the Thermoascus aurantiacus or Aspergillus oryzae metalloprotease.

In another embodiment, a metalloprotease has an amino acid sequence that differs by ten, or by nine, or by eight, or by seven, or by six, or by five amino acids from amino acids −178 to 177, −159 to 177, or +1 to 177 of the amino acid sequences of these metalloproteases, e.g., by four, by three, by two, or by one amino acid.

In particular embodiments, the metalloprotease a) comprises or b) consists of
i) the amino acid sequence of amino acids −178 to 177, −159 to 177, or +1 to 177 of SEQ ID NO:1 of WO 2010/008841;
ii) the amino acid sequence of amino acids −23-353, −23-374, −23-397, 1-353, 1-374, 1-397, 177-353, 177-374, or 177-397 of SEQ ID NO: 3 of WO 2010/008841;
iii) the amino acid sequence of SEQ ID NO: 5 of WO 2010/008841; or
allelic variants, or fragments, of the sequences of i), ii), and iii) that have protease activity.

A fragment of amino acids −178 to 177, −159 to 177, or +1 to 177 of SEQ ID NO: 1 of WO 2010/008841 or of amino acids −23-353, −23-374, −23-397, 1-353, 1-374, 1-397, 177-353, 177-374, or 177-397 of SEQ ID NO: 3 of WO 2010/008841; is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

In another embodiment, the metalloprotease is combined with another protease, such as a fungal protease, preferably an acid fungal protease.

Commercially available products include ALCALASE®, ESPERASE™, FLAVOURZYME™, NEUTRASE®, RENNILASE®, NOVOZYM™ FM 2.0L, and iZyme BA (available from Novozymes A/S, Denmark) and GC106™ and SPEZYME™ FAN from Genencor International, Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

Trehalases

Trehalases are enzymes which degrade trehalose into its unit monosaccharides (i.e., glucose). According to the invention trehalase may be one single trehalase, or a combination of two of more trehalases of any origin, such as plant, mammalian, or microbial origin, such a bacterial or fungal origin. In an embodiment the trehalase is of mammalian origin, such as porcine trehalase. In a preferred embodiment the trehalase is of fungal origin, preferably of yeast origin. In an embodiment the trehalase is derived from a strain of Saccharomyces, such as a strain of Saccharomyces cervisae. In a preferred embodiment the trehalase is derived from a strain of Trichoderma, such as a strain of Trichoderma reesei, e.g., the one disclosed in SEQ ID NO: 12 herein.

Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet, e.g., on "expasy.org/enzyme/". Trehalases are enzymes that catalyze the following reactions:

EC 3.2.1.28:

Alpha,alpha-trehalose+$H_2O$=2 D-glucose;

EC 3.2.1. 93:

Alpha,alpha-trehalose 6-phosphate+$H_2O$<=>D-glucose+D-glucose 6-phosphate;

The two enzyme classes are both referred to as "trehalases" in context of the present invention. In a preferred embodiment the trehalase is classified as EC 3.2.1.28. In another embodiment the trehalase is classified as EC 3.2.1.93. In embodiment the trehalase is a neutral trehalase. In another embodiment the trehalase is an acid trehalase.

Examples of neutral trehalases include, but are not limited to, treahalases from *Saccharomyces cerevisiae* (Londesborouh et al. (1984) Characterization of two trehalases from baker's yeast" Biochem J 219, 511-518; *Mucor* roxii (Dewerchin et al (1984), "Trehalase activity and cyclic AMP content during early development of *Mucor rouxii* spores", J. Bacteriol. 158, 575-579); *Phycomyces blakesleeanus* (Thevelein et al (1983), "Glucose-induced trehalase activation and trehalose mobilization during early germination of *Phycomyces blakesleeanus* spores" J. Gen Microbiol. 129, 719-726); *Fusarium oxysporium* (Amaral et al (1996), "Comparative study of two trehalase activities from *Fusarium oxysporium* var *Linii*" Can. J Microbiol. 41, 1057-1062);

Examples of neutral trehalases include, but are not limited to, trehalases from *Saccharomyces cerevisiae* (Parvaeh et al. (1996) Purification and biochemical characterization of the ATH1 gene product, vacuolar acid trehalase from *Saccharomyces cerevisae*" FEBS Lett. 391, 273-278); *Neorospora crassa* (Hecker et al (1973), "Location of trehalase in the ascospores of *Neurospora*: Relation to ascospore dormancy and germination". J. Bacteriol. 115, 592-599); *Chaetomium aureum* (Sumida et al. (1989), "Purification and some properties of trehalase from *Chaetomium aureum* MS-27. J. Ferment. Bioeng. 67, 83-86); *Aspergillus nidulans* (d'Enfert et al. (1997), "Molecular characterization of the *Aspergillus nidulans* treA gene encoding an acid trehalase required for growth on trehalose. Mol. Microbiol. 24, 203-216); *Humicola grisea* (Zimmermann et al. (1990)." Purification and properties of an extracellular conidial trehalase from *Humicola grisea* var. *thermoidea*", Biochim. Acta 1036, 41-46); *Humicola grisea* (Cardello et al. (1994), "A cytosolic trehalase from the thermophilhilic fungus *Humicola grisea* var. *thermoidea*', Microbiology UK 140, 1671-1677; *Scytalidium thermophilum* (Kadowaki et al. (1996), "Characterization of the trehalose system from the thermophilic fungus *Scytalidium thermophilum*" Biochim. Biophys. Acta 1291, 199-205); and *Fusarium oxysporium* (Amaral et al (1996), "Comparative study of two trehalase activities from *Fusarium oxysporium* var *Linii*" Can. J Microbiol. 41, 1057-1062).

A trehalase is also know from soybean (Aeschbachet et al (1999) "Purification of the trehalase GmTRE1 from soybean nodules and cloning of its cDNA", Plant Physiol 119, 489-496).

Trehalases are also present in small intestine and kidney of mammals.

Commercially available trehalase includes the porcine trehalase available from SIGMA, USA (product #A8778).

The trehalase may be added or present in any effective dosage together with the cellulolytic composition during presaccharification, or saccharification and/or fermentation, which includes, but is not limited to, from 1 to 500 Sigma units per liter fermentation medium, preferably 10-100 Sigma units per liter fermentation medium.

Materials & Methods

Cellulase A:

Cellulolytic composition derived from *Trichoderma reesei* (CELLUCLAST™ 1.5L, Novozymes)

Cellulase B:

Cellulolytic composition derived from *Trichoderma reesei* comprising GH61A polypeptide having cellulolytic enhancing activity derived from a strain of *Thermoascus aurantiacus* (SEQ ID NO: 2 in WO 2005/074656); *Aspergillus oryzae* beta-glucosidase (fusion protein disclosed in WO 2008/057637); and *Aspergillus aculeatus* xylanase (disclosed in WO 94/21785 as SEQ ID NO: 5 (referred to as Xyl II).

Cellulase C:

Cellullolytic composition derived from *Trichoderma reesei* comprising *Thermoascus aurantiacus* GH61A polypeptide having cellulolytic enhancing activity (SEQ ID NO: 2 in WO 2005/074656), *Aspergillus fumigatus* beta-glucosidase (SEQ ID NO: 2 in WO 2005/047499 or SEQ ID NO: 6 herei).

Cellulase D:

Cellulolytic composition derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 8 herein), *Aspergillus fumigatus* beta-glucosidase (SEQ ID NO: 2 in WO 2005/047499 or SEQ ID NO: 6 herein) variant F100D, S283G, N456E, F512Y) disclosed in WO 2012/044915 or co-pending PCT application PCT/US11/054185; *Aspergillus fumigatus* Cel7A CBH1 disclosed as SEQ ID NO: 6 in WO2011/057140 and SEQ ID NO: 2 herein and *Aspergillus fumigatus* CBH II disclosed as SEQ ID NO: 18 in WO 2011/057140 and as SEQ ID NO: 4 herein.

Glucoamylase E:

Glucoamylase derived from *Talaromyces emersonii* disclosed in WO 99/28448 or SEQ ID NO: 9 herein, *Trametes cingulata* glucoamylase disclosed as SEQ ID NO: 2 in WO 06/69289 or SEQ ID NO: 10 herein, and *Rhizomucor pusillus* alpha-amylase with *Aspergillus niger* glucoamylase linker and SBD disclosed as V039 in Table 5 in WO 2006/069290 or SEQ ID NO: 11 herein (ratio between components about 65:15:1).

Glucoamylase E2:

Glucoamylase derived from *Talaromyces emersonii* disclosed in WO 99/28448 or SEQ ID NO: 9 herein, *Trametes cingulata* glucoamylase disclosed as SEQ ID NO: 2 in WO 06/69289 or SEQ ID NO: 10 herein, and a *Rhizomucor pusillus* alpha-amylase variant (AA PE96) with *Aspergillus niger* glucoamylase linker and SBD disclosed as V039 in Table 5 in WO 2006/069290 or SEQ ID NO: 11 herein with the following mutations: G128D+D143N using SEQ ID NO: 11 for numbering (ratio between components about 25:6:1).

Trehalase from *Trichoderma reesei* is shown in SEQ ID NO: 12 herein

Yeast: ETHANOL RED (Fermentis)

Methods

Glucoamylase Activity (AGU)

Glucoamylase activity may be measured in Glucoamylase Units (AGU).

The Novo Glucoamylase Unit (AGU) is Defined as the Amount of Enzyme, which Hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Acid Alpha-Amylase Activity

Determination of FAU-F

FAU(F) Fungal alpha-amylase Units (Fungamyl) is measured relative to an enzyme standard of a declared strength. The assay substrate is 4,6-ethylidene(G7)-p-nitrophenyl (G1)-alpha,D-maltoheptaoside (ethylidene-G7-PNP).

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Determination of AFAU

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

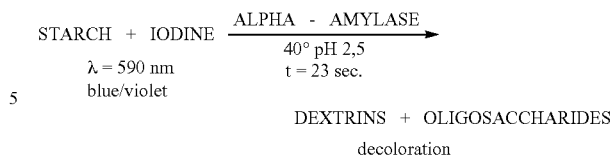

Standard Conditions/Reaction Conditions:

| Substrate: | Soluble starch, approx. 0.17 g/L |
|---|---|
| Buffer: | Citrate, approx. 0.03M |
| Iodine (I2): | 0.03 g/L |
| CaCl2: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Protease Activity (AU)

The protease activity may be determined with denatured hemoglobin as substrate. In the Anson-Hemoglobin method for the determination of protease activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milliequivalent of tyrosine.

A folder AF 4/5 describing the analytical method in more detail is available upon request to Novozymes A/S, Denmark, which folder is hereby included by reference.

SIGMA™ Enzymatic Assay for Trehalase

One SIGMA unit will convert 1.0 micro mol of trehalose to 2.0 micro mol of glucose per minutes at pH 5.7 at 37° C. (liberated glucose determined at pH 7.5).

Determination of Relative ED50

The Relative ED50 (half maximal hydrolysis loading value) is determined as described in Example 3 using Graphpad Prism 3.0 software or a new version or another similar software.

EXAMPLES

Example 1

Ethanol Yield for Four Cellulolytic Compositions Added During SSF

Industrially produced corn mash from East Kansas Agri-Energy was used for all samples. A 5 gallon container containing the liquefied mash was thawed, partitioned into smaller quantities (1 liter screw top Nalgene bottles) and refrozen. One liter of this mash was thawed for about 4 hours prior to starting this study. The mash was supplemented with 3 ppm penicillin and 1000 ppm urea using solutions of 1 g/l penicillin and 200 g/L urea, respectively, and adjusted to pH 5.0 with 40% $H_2SO_4$. The dry solids content of the mash was measured on a Mettler-Toledo moisture balance (HB43-S halogen), with a resulting value of 33.% DS. Approximately 5 g of the industrial mash was added to 15 ml conical centrifuge tubes with flip tops (NUNC #362694). A total of 212 fermentations were run. Enzymes were dosed according to the dosing specifications in the following table and the volume of stock solution to add to fermentation was determined using the equation:

$$Enz.\ dose\ (ml) = \frac{Final\ enz.\ dose\ (mgEP/g\ DS) \times Mash\ weight(g) \times Solid\ content\ (\%\ DS)}{Conc.\ enzyme\ (mg\ EP/ml)}$$

| | Enzyme | Dose range | Units |
|---|---|---|---|
| 1 | Glucoamylase E | 0.056% | w/w % product/g DS |
| 2 | Cellulase A (Celluclast 1.5L) | 5, 10, 30, 60, 120, 250, 500, 750, 1000, 1500, 2000, 3000, 5000 | micrograms EP/g DS |
| 3 | Cellulase B | | |
| 4 | Cellulase C | | |
| 5 | Cellulase D | | |

Glucoamylase E was added to all samples, and one dose of Cellulase was then dosed on to top of this background. Water was dosed into each sample such that the total added volume of enzyme and water was approximately 400 microliters/5 g sample to yield a final % DS of 30%. Rehydrated yeast (5.5 g Fermentis Ethanol Red yeast in 100 mL 35° C. tap water incubated at 32° C. for 30 minutes) was dosed at 110 microliters of yeast solution in each 5 g sample. Tubes were weighed at time 0 and then fermented for 52 hours at 32° C.

HPLC analysis

At the end of the fermentation time point, 50 microliters of 40% $H_2SO_4$ was added to each sample and vortexed to ensure mixing. Samples were centrifuged at 1570×g (3000 rpm) for 10 minutes in a Beckman Coulture benchtop centrifuge (Allegra 6R) with rotor GH3.8 and then filtered into HPLC vials through 0.45 micron syringe filters (Whatman) prior to submission for HPLC analysis.
HPLC system: Agilent's 1100/1200 series with Chem station software
Degasser
Quadratic Pump
Auto-Sampler
Column Compartment/w Heater
Refractive Index Detector (RI)
Column: Bio-Rad HPX-87H Ion Exclusion Column 300 mm×7.8 mm parts#125-0140
Bio-Rad guard cartridge cation H parts#125-0129, Holder parts#125-0131
Method: 0.005 M $H_2SO_4$ mobile phase
Flow rate of 0.6 ml/min
Column temperature –65° C.
RI detector temperature –55° C.

The method quantifies several analytes using calibration standards for dextrins (DP4+), maltotriose, maltose, glucose, fructose, acetic acid, lactic acid, glycerol and ethanol. A 4 point calibration including the origin is used.

The results of ethanol yield and increases over the control at 52 hours of fermentation are summarized in FIG. 1.

The results show that all four cellulases (cellulolytic compositions) give a significant additional ethanol yield benefit when added in an SSF on top of Glucoamylase E. Although Cellulase A gives more than 1% ethanol increase at a dosing of 3000 microgram EP/gDS, it is inferior compared to Cellulase B, C and D. At 5000 microgram EP/gDS Cellulase B is delivering a 3.8% ethanol yield increase. Cellulase C and D result in ethanol yields of 5.8-6.0%, respectively, at a dosing of 5000 microgram EP/gDS.

The results show that cellulolytic compositions for hydrolyzing cellulosic feed stocks give significantly increased ethanol yields when applied during fermentation together with glucoamylase on liquefied corn mash at concentrations significantly lower than the 3 to 10 milligram EP/g cellulose dosing of these cellulase complexes in the hydrolysis of lignocelluloses.

Example 2

Determination of Relative ED50 loading value and specific activity of wild-type Aspergillus fumigatus GH3A beta-glucosidase (SEQ ID NO: 6) and variant F100D+S283G+N456E+F512Y Pretreatment of Corn Stover (PCS):

Corn stover was pretreated at the U.S. Department of Energy National Renewable Energy Laboratory (NREL) using 1.4% (w/v) sulfuric acid for 2 minutes at 190° C. The water-insoluble solids in the pretreated corn stover (PCS) contained 57.5% cellulose, 4.6% hemicelluloses, and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

The pretreated corn stover was washed repeatedly using reverse osmosis water followed by decanting off the supernatant fraction, until the measured pH was greater than 4.0. The washed pretreated corn stover (initial dry weight 32.35% TS) was subsequently milled prior to use in a Cosmos ICMG 40 wet multi-utility grinder (EssEmm Corporation, Tamil Nadu, India). The dry weight of the milled, water-washed pretreated corn stover was 7.4% TS.

In accordance with the Examples in WO 2012/044915 wild-type Aspergillus fumigatus GH3A beta-glucosidase (SEQ ID NO: 6 herein) and variant F100D+S283G+N456E+F512Y (Variant 1), was contructed and purified. They were evaluated for their ability to enhance the hydrolysis of PCS by a Trichoderma reesei cellulolytic protein preparation composed of CELLUCLAST® 1.5L (Novozymes A/S, Bagsvaerd, Denmark) supplemented with 10% addition of *Thermoascus aurantiacus* GH61A polypeptide having cellulolytic enhancing activity (obtained as described in WO 2005/074656) and 2% addition of SHEARZYME® 2× (Novozymes A/S, Bagsvaerd, Denmark), hereinafter designated "*Trichoderma reesei* cellulolytic protein composition".

The hydrolysis of PCS was conducted using 2.2 ml deep-well plates (Axygen, Union City, Calif., USA) in a total reaction volume of 1.0 ml. The hydrolysis was performed with 50 mg of washed, ground, sieved PCS per ml of 50 mM sodium acetate pH 5.0 buffer containing 1 mM manganese sulfate, 40 g of glucose per ml, and a fixed protein loading of 2.24 mg of the *T. reesei* cellulolytic composition per gram of cellulose and between 0 to 10% addition (by protein) to the base CELLUCLAST 1.5L enzyme loading with the purified *Aspergillus fumigatus* Family 3A beta-glucosidase (2.24 mg of the *T. reesei* cellulolytic composition per g of cellulose and between 0 and 0.2 mg of *Aspergillus fumigatus* Family 3A beta-glucosidase or variant thereof per g of cellulose). Hydrolysis assays were performed in triplicate for 72 hours at 50° C. Following hydrolysis, samples were filtered with a 0.45 µm MULTI-SCREEN® 96-well filter plate (Millipore, Bedford, Mass., USA) and filtrates analyzed for sugar content as described below. When not used immediately, filtered sugary aliquots were frozen at −20° C.

Sugar concentrations of samples diluted in 0.005 M $H_2SO_4$ were measured after elution by 0.005 M H2SO4 with 0.05% w/w benzoic acid at a flow rate of 0.6 ml per minute from a 4.6×250 mm AMINEX® HPX-87H column (Bio-Rad Laboratories, Inc., Hercules, Calif., USA) at 65° C. with quantitation by integration of glucose and cellobiose signals from refractive index detection (CHEMSTATION®, AGILENT® 1100 HPLC, Agilent Technologies, Santa Clara, Calif., USA) calibrated by pure sugar samples. The resultant equivalents were used to calculate the percentage of cellulose conversion for each reaction.

Glucose released was calculated by subtracting glucose levels measured in the PCS alone from those measured in PCS with enzyme mixture.

Figure 2:
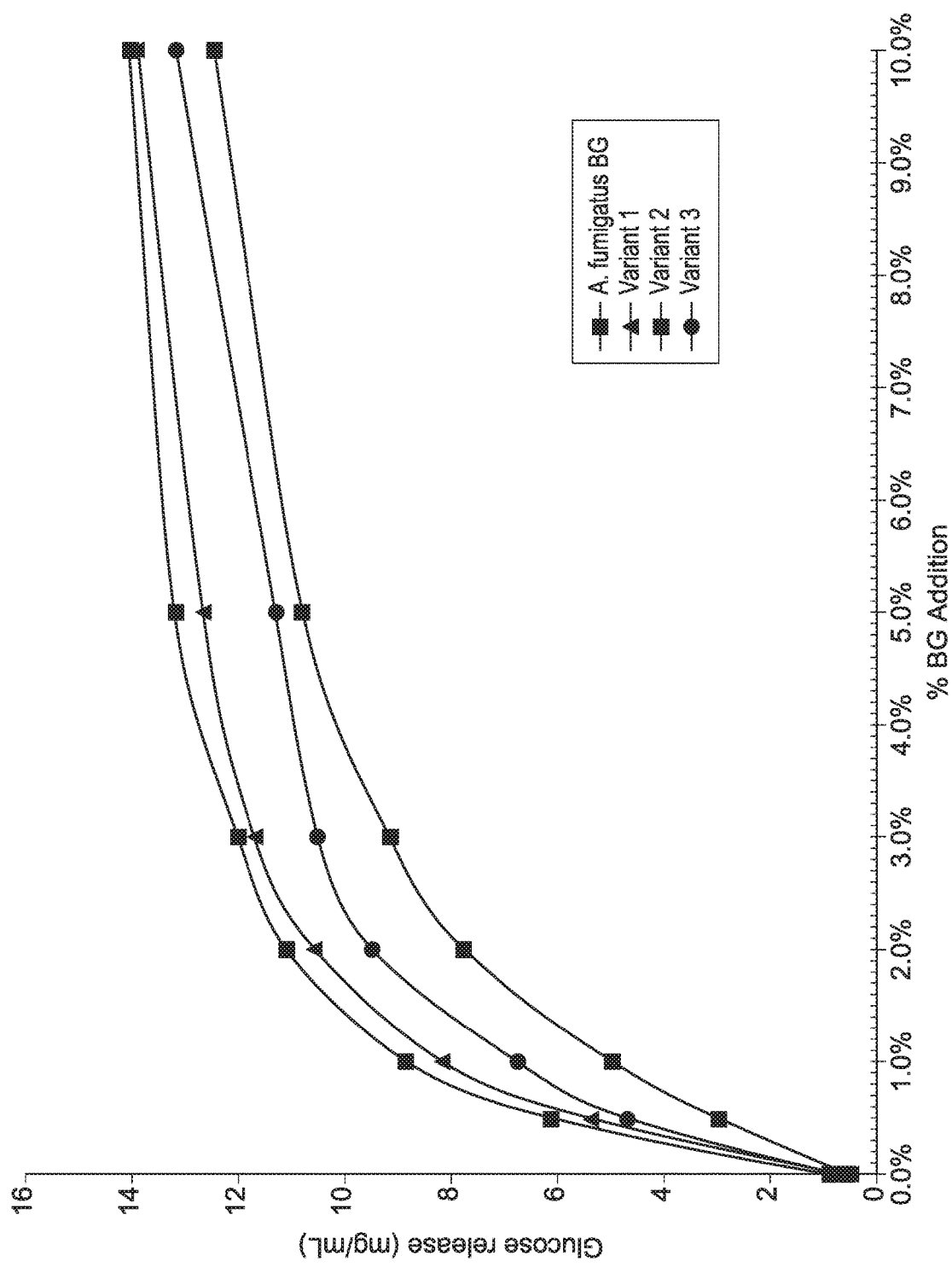
FIG. 2 shows net glucose production of a *Trichoderma reesei* cellulolytic composition with varying concentrations of wild-type *Aspergillus fumigatus* Family GH3A beta-glucosidase, variant L89M+G91L+F100D+I140V+I186V+ S283G+N456E+F512Y, variant L89M+G91L+I140V+ I186V, and variant F100D+S283G+N456E+F512Y.

The results shown in FIG. 2 demonstrated that the *Aspergillus fumigatus* beta-glucosidase variant F100D+S283G+N456E+F512Y (Variant 1) has a higher specific activity than the wild-type *Aspergillus fumigatus* beta-glucosidase (releases more glucose at a given enzyme concentration than the wild-type enzyme at the same concentration under the specified conditions).

The Relative ED50 (half maximal hydrolysis loading value) for the wild-type and Variant 1 are shown in the table below Example 3.

Example 3

Determination of Relative ED50 Loading Value and Specific Activity of *Aspergillus fumigatus* Family GH3A beta-glucosidase variant L89M+G91L+F100D+I140V+I186V+S283G+N456E+F512Y, variant L89M+G91L+I140V+I186V, and variant F100D+S283G+N456E+F512Y In accordance with Example 2 herein and the Examples in WO 2012/044915 purified wild-type *Aspergillus fumigatus* Family GH3A beta-glucosidase and variant F100D+S283G+N456E+F512Y (Variant 1), and variant L89M+G91L+F100D+I140V+I186V+S283G+N456E+F512Y (Variant 2) and variant L89M+G91L+I140V+I186V (Variant 3), were evaluated for their ability to enhance the hydrolysis of PCS by the "*Trichoderma reesei* cellulolytic composition" (Example 2).

The hydrolysis of PCS and the analysis thereof was performed according to the procedure described in Example 2.

The results shown in FIG. 2 demonstrated that all the variants of the *A. fumigatus* Family GH3A beta-glucosidase have a higher specific activity than the wild-type beta-glucosidase (releases more glucose at a given enzyme concentration than the wild-type enzyme at the same concentration under the specified conditions).

The Relative ED50 (half maximal hydrolysis loading value) shown in the table below was calculated using Graphpad Prism 3.0 software. The built-in function for one site binding was used. Bmax was used to measure maximum hydrolysis and Kd as $ED_{50}$. This was done without weighting (minimization of absolute distances squared). The Relative ED50 loading values were calculated from the determined ED50 loading values setting the Relative ED50 loading value for the wild-type *Aspergillus fumigatius* beta-glucosidase to 1.00.

For instance, Variant 1 only needs 0.45 times the wild-type loading (% BG Addition in FIG. 2) to provide the same glucose release (mg/ml) as the wild-type after half maximal hydrolysis loading.

| *Aspergillus fumigatus* beta-glucosidase | Mutations | Relative ED50 |
|---|---|---|
| Wild-type (SEQ ID NO: 6) | — | 1.00 |
| Variant 1 | F100D + S283G + N456E + F512Y | 0.45 |
| Variant 2 | L89M + G91L + F100D + I140V + I186V + S283G + N456E + F512Y | 0.37 |
| Variant 3 | L89M + G91L + I140V + I186V | 0.56 |

Example 4

Ethanol Yield when Adding Cellulolytic Composition and Glucoamylase During Pre-Saccharification or Saccharification All treatments were evaluated via 5 g small assay. Industrially produced corn mash from IGPC Ethanol Inc (ON, Canada) was used for all tests. The dry solid (DS) of the corn mash was 32.2%, and 200 g of corn mash was supplemented with 0.6 ml of 1 g/L penicillin and 1 ml of 200 g/L of urea. The pH of this slurry was adjusted to 5.0 with 40% $H_2SO_4$. The final dry solid of the corn mash was determined to be 31.95%. Approximately 5 g of this slurry was added to 15 ml polypropylene tube. The tubes were prepared by drilling a ¹⁄₃₂ inch (1.5 mm) hole and the empty tubes were then weighed before corn slurry was added. The tubes were weighed again after the mash was added to determine the exact weight of mash in each tube. Each tube was dosed with the appropriate amount of enzyme as shown in the Table below. Actual enzyme dosages were based on the exact weight of corn slurry in each tube. The tubes for pre-saccharification were placed in 50° C. air shaker (no shaking) for 4 hours before moving to 32° C. water bath for SSF. The tubes not being pre-saccharificied were dosed with 100 micro liter of yeast (ETHANOL RED) propagate to around 5 g corn mash, and then were incubated in 32° C. water bath for SSF. After 4 hours of pre-saccharification, the tubes in Treatments 1 to 3 were taken out of the air shaker and placed into 32° C. water bath to cool down for half hour (30 minutes), and the yeast propagate was then dosed for SSF. Five replicates of each treatment were run. Samples were taken at 54 hour of fermentation for HPLC analysis. The HPLC preparation consisted of stopping the reaction by addition of 50 micro liters of 40% $H_2SO_4$, centrifuging, and filtering through a 0.45 micrometer filter. Samples were stored at 4° C. until analysis. Agilent™ 1100 HPLC system coupled with RI detector was used to determine ethanol and oligosaccharides concentration. The separation column was aminex HPX-87H ion exclusion column (300 mm×7.8 mm) from BioRad™.

| | Treatments | Pre-sacch | GA dose (AGU/g DS) | Cellulase dose (ugEP/gDS) |
|---|---|---|---|---|
| 1 | Glucoamylase E2 | yes | 0.60 | — |
| 2 | Glucoamylase E2 + Cellulase A (Celluclast 1.5L) | yes | 0.60 | 100 |
| 3 | Glucoamylase E2 + Cellulase D | yes | 0.60 | 100 |
| 4 | Glucoamylase E2 | no | 0.60 | — |
| 5 | Glucoamylase E2 + Cellulase A (Celluclast 1.5L) | no | 0.60 | 100 |
| 6 | Glucoamylase E2 + Cellulase D | no | 0.60 | 100 |

Results

The results from HPLC were summarized in the table below. Glucoamylase E2, together with Ccellulase A showed better performance in pre-saccharification compared to conventional SSF process with Glucoamylase E. The presence of Cellulase D showed better performance than Cellulase A (CELLUCLAST™ 1.5L) in both cases.

| | Treatment | Ethanol (% w/v) | Ethanol Increase |
|---|---|---|---|
| 1 | Glucoamylase E2 | 12.51 | — |
| 2 | Glucoamylase E2 (pre-sacch) | 12.52 | 0.10% |
| 3 | Glucoamylase E2 + Cellulase A (Celluclast™ 1.5L) | 12.57 | 0.55% |
| 4 | Glucoamylase E2 + Cellulase A (Celluclast™ 1.5L) (pre-sacch) | 12.62 | 0.92% |
| 5 | Glucoamylase E2 + Cellulase D | 12.64 | 1.05% |
| 6 | Glucoamylase E2 + Cellulase D (pre-sacch) | 12.66 | 1.26% |

Example 5

Effect of Adding Cellulolytic Composition and Trehalase During SSF

All treatments were evaluated via 5 g small assay. Industrially produced corn mash from BioFuel Energy (Fairmont, Minn.) was used for this test. 500 g of corn mash was supplemented with 1.5 mL of 1 g/L penicillin and 2.5 mL of 200 g/L urea. The pH of this slurry was adjusted to 5.0 with 40% $H_2SO_4$. The final dry solid of the corn mash was determined to be 31.43%. Approximately 5 g of this slurry was added to a 15 mL polypropylene tube. The tubes were prepared by drilling a 1/32 inch (1.5 mm) hole and the empty tubes were then weighed before corn slurry was added. The tubes were weighed again after the mash was added to determine the exact weight of mash in each tube. Each tube was dosed with the appropriate amount of enzyme as shown in the Table below. Actual enzyme dosages were based on the exact weight of corn slurry in each tube. The tubes were then dosed with 100 microL rehydrated ETHANOL RED™ yeast (yeast rehydrated by placing 5.5 g of yeast in 100 mL of 32° C. tap water for 30 minutes with magnetic stirring), and were then incubated in 32° C. water bath for SSF. Three replicates of each treatment were run. Samples were taken after 54 hour of fermentation for HPLC analysis. The HPLC preparation consisted of stopping the reaction by addition of 50 microL of 40% $H_2SO_4$, centrifuging, and filtering through a 0.45 micrometer filter. Samples were stored at 4° C. until analysis. Agilent™ 1100 HPLC system coupled with RI detector was used to determine ethanol and oligosaccharides concentration. The separation column was aminex HPX-87H ion exclusion column (300 mm×7.8 mm) from BioRad™.

| Treatment # | Name | GA dose (AGU/g DS) | Cellulase dose (µg EP/g DS) | Trehalase Dose (µg EP/g DS) |
|---|---|---|---|---|
| 1 | Glucoamylase E2 | 0.6 | 0 | 0 |
| 2 | Glucoamylase E2 + Cellulase D | 0.6 | 250 | 0 |
| 3 | Glucoamylase E2 + Cellulase D + Trehalase (5) | 0.6 | 250 | 5 |
| 4 | Glucoamylase E2 + Cellulase D + Trehalase (20) | 0.6 | 250 | 20 |
| 5 | Glucoamylase E2 + Cellulase D + Trehalase (100) | 0.6 | 250 | 100 |

Results

The results from HPLC are summarized in the Table below. The results show that addition of Cellulase D (cellulolytic composition) to the Glucoamylase E–only (control) significantly increased the final ethanol titer. Furthermore, addition of 20 and 100 micro g EP/g DS trehalase to the Glucoamylase E+Cellulase D treatment significantly increased ethanol titers over the Glucoamylase E+Cellulase D control.

| Treatment # | Name | Ethanol (% w/v) | Ethanol Increase | T-K* |
|---|---|---|---|---|
| 1 | Glucoamylase E2 | 11.61 | — | A |
| 2 | Glucoamylase E2 + Cellulase D | 11.80 | 1.64% | B |
| 3 | Glucoamylase E2 + Cellulase D + Trehalase (5) | 11.78 | 1.46% | B |
| 4 | Glucoamylase E2 + Cellulase D + Trehalase (20) | 11.88 | 2.35% | C |
| 5 | Glucoamylase E2 + Cellulase D + Trehalase (100) | 11.89 | 2.43% | C |

*Ethanol concentration results were analyzed in by the Tukey-Kramer HSD test to determine significant differences among amylases. In each T-K column, levels not sharing a letter are significantly different.

Example 6

Effect of Adding Cellulolytic Composition During SSF on Backend Dewatering

Fermentation:

Industrially produced corn mash from Platinum Ethanol was used for all samples. A 5 gallon container containing the liquefied mash was thawed, partitioned into smaller quantities (1 liter screw top Nalgene bottles) and refrozen. One liter of this mash was thawed for about 4 hours prior to starting this study. The mash was supplemented with 3 ppm penicillin and 1000 ppm urea using solutions of 1 g/l penicillin and 200 g/L urea, respectively, and adjusted to pH 5.0 with 40% $H_2SO_4$. The dry solids content of the mash was measured on a Mettler-Toledo moisture balance (HB43-S halogen), with a resulting value of 31.08% DS. Approximately 25 g of the industrial mash was added to 50 ml conical centrifuge tubes with screw tops (VWR 89039-660). A total of 24 fermentations were run. Enzymes were dosed according to the dosing specifications in Table 1 below and the volume of stock solution to add to fermentation was determined using the equation:

$$Enz.\ dose\ (ml) = \frac{Final\ enz.\ dose\ (mg\ EP/g\ DS) \times Mash\ weight(g) \times Solid\ content\ (\%\ DS)}{Conc.\ enzyme\ (mg\ EP/ml)}$$

TABLE 1

Enzyme treatments tested

| | Enzyme | Dose | Units |
|---|---|---|---|
| 1 | Glucoamylase E2 | 0.6 | AGU/gDS |
| 2 | Cellulase D | 0, 10, 30, 60, 100, 250 | micro g/gDS |

Glucoamylase E2 was added to all samples, and one dose of Cellulase D was then dosed on top of this background. Four replicates were performed per treatment. Water was dosed into each sample such that the total added volume of enzyme and water was approximately 285 microliters/25 g sample to yield a final % DS of 30.7%. Rehydrated yeast (5.5 g Fermentis Ethanol Red yeast in 100 mL 35° C. tap water incubated at 32° C. for 30 minutes) was dosed at 250 microliters of yeast solution in each 25 g sample. Tubes were weighed at time 0 and then fermented for 72 hours at 32° C.

Distillation:

All Samples were Distilled to Remove Ethanol and Generate Whole Stillage. A Büchi Multivapor evaporation system was used for all distillations. The unit distilled 12 samples at a time, so two replicates from each of the six treatments were distilled in each distillation set. The parameters used are shown in Table 2. Tubes were weighed after distillation and weight lost during distillation was replaced with DI water. Tubes were weighed again after water addition.

TABLE 2

Distillation parameters

| | |
|---|---|
| Time | 80 min |
| Temperature | 75° C. |
| Vacuum | 200-153 mBar (40 min) |
| | 153-148 mBar (40 min) |
| RPM | 8 |

Dewatering Assay: After distillation, the samples were centrifuged 6 at a time at 1,400×g for 10 minutes in an Avanti J-E series centrifuge with a JS-5.3 rotor (Beckman Coulter). Following centrifugation the samples were immediately decanted into pre-weighed 15 mL conical tubes (NUNC #362694). Weights of the resulting wet cake and thin stillage were recorded. Wet cake was placed in pre-weighed drying pans and incubated at 55° C. overnight and transferred to 105° C. for 2 hours. Weights were recorded before and after incubations. These values were used to calculate dry solids values using the following formula:

$$\%\ DS = \frac{g\ drysample}{g\ wet\ sample} * 100\%$$

Results:

Data from the dewatering assay were loaded into JMP 9.0.2 for statistical analysis. The Fit Model platform was used in order to perform a Standard Least Squares fit on the data. Model effects included cellulolytic composition Dose effects up to the fourth power, a Set effect to indicate the distillation grouping of each tube, and crossed effects between Set and Dose up to the fourth power. The model was generated, and insignificant effects were removed one at a time, starting with the highest order insignificant effect and performing the fit again after each removal.

Figure 3:
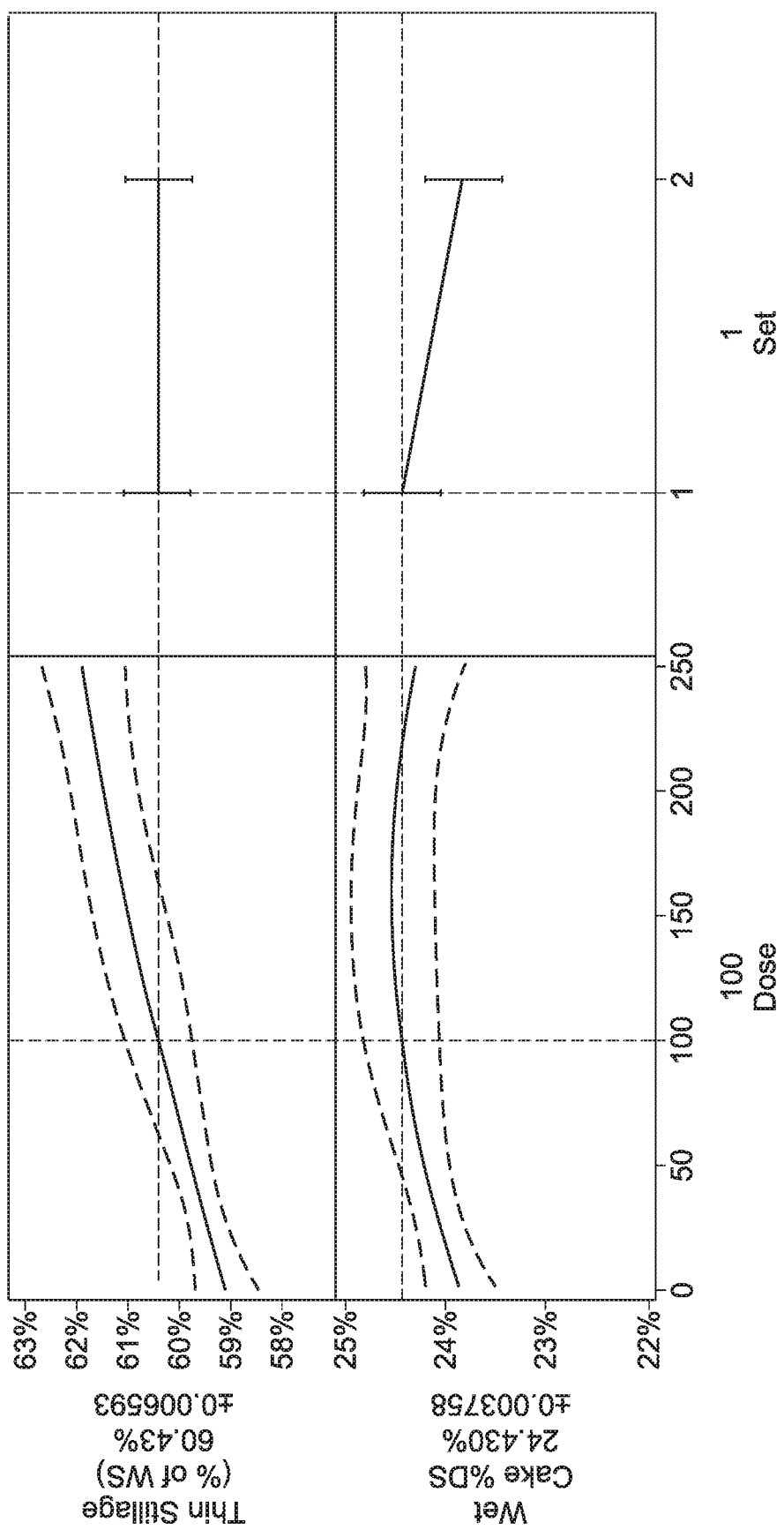
FIG. 3: Set 1 thin stillage mass and wet cake % DS models. The increasing trend of thin stillage mass vs cellulolytic composition dose indicates that increased water was shifted to the thin stillage under cellulase treatment.
Figure 4:
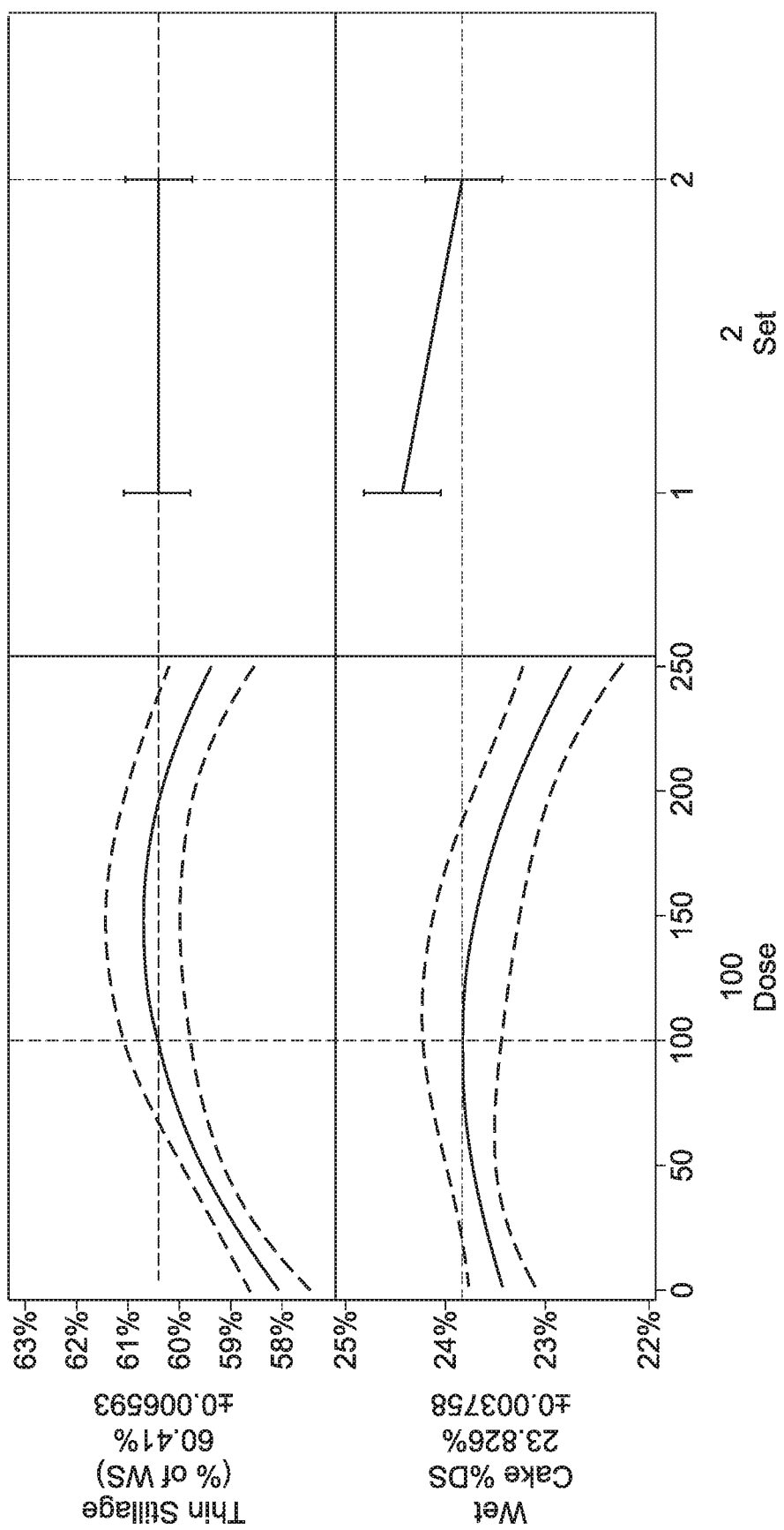
FIG. 4: Set 2 thin stillage mass and wet cake % DS models. The increasing trend of thin stillage mass vs dose indicates that increased water was shifted to the thin stillage under cellulolytic composition treatment, with effect saturation around 100 micro g/gDS.

Following this process, the model was simplified to the following effects:
Dose
Dose*Dose
Set
Dose*Set
Dose*Dose*Set The model for thin stillage mass indicates that cellulase treatment significantly increases the percent of whole stillage mass that is carried with the thin stillage after solid/liquid separation (FIGS. 3 and 4). This response increases through a cellulolytic composition dose of about 100 micro g/gDS, then probably levels off through 250 microg/gDS, based on the disagreement between Sets 1 and 2. At 100 microg/gDS, this effect increases the thin stillage partitioning rate over control by 2.2% and 4% for Sets 1 and 2, respectively. Wet cake % DS slightly increases or remains the same, indicating that much of the mass shifted to the thin stillage is water. If the cellulolytic composition did not have a dewatering effect, and instead merely solubilized solids into the thin stillage, the wet cake % DS should have decreased.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The present invention is further described in the following numbered paragraphs:

1. A process of producing a fermentation product, comprising
(a) liquefying a starch-containing material with an alpha-amylase;
optionally pre-saccharifying the liquefied material before step (b);
(b) saccharifying the liquefied material;
(c) fermenting using a fermentation organism;
wherein a carbohydrate-source generating enzyme and/or a cellulolytic composition are present or added during the optional presaccharification step, saccharification step (b), and/or fermentation step (c), or simulataneous saccharification and fermentation.

2. The process of paragraph 1, wherein the cellulolytic composition is derived from *Trichoderma reesei, Humicola insolens* or *Chrysosporium lucknowense*.

3 The process of paragraph 1 or 2, wherein the cellulolytic composition comprising a beta-glucosidase, a cellobiohydrolase, and an endoglucanase.

4. The process of any of paragraphs 1-3, wherein the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

5. The process of any of paragraphs 1-4, wherein the carbohydrate-source generating enzyme is a glucoamylase, preferably a combination of glucoamylase and alpha-amylase.

6. The process of paragraph 5, wherein the glucoamylase is of fungal origin, preferably from a strain of *Aspergillus*, preferably *A. niger, A. awamori*, or *A. oryzae*; or a strain of *Trichoderma*, preferably *T. reesei*; or a strain of *Talaromyces*, preferably *Talaromyces emersonii*.

7. The process of any of paragraphs 5-7, wherein the alpha-amylase is derived from a strain of the genus *Rhizomucor*, preferably a strain the *Rhizomucor pusillus*, or the genus *Meripilus*, preferably a strain of *Meripilus giganteus*.

8. The process of paragraph 7, wherein the alpha-amylase is derived from a *Rhizomucor pusillus* and has *Aspergillus niger* glucoamylase linker and starch-binding domain (SBD) and comprises at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P2190+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 11 for numbering).

9. The process of any of paragraphs 1-8, wherein the carbohydrate-source generating enzyme and/or the cellulolytic composition are added during a pre-saccharification step carried out before saccharification step (b) and/or fermentation step (c).

10. The process of any of paragraphs 1-13, wherein the carbohydrate-source generating enzyme and the cellulolytic composition are added during a pre-saccharification step carried out before simultaneous saccharification and fermentation (SSF).

11. The process of any of paragraphs 1-10, comprising
(a) liquefying a starch containing material with an alpha-amylase;
presaccharifying the liquefied material using a carbohydrate-source generating enzyme and a cellulolytic composition;
(b) saccharifying;
(c) fermenting using a fermentation organism;
wherein saccharification step (b) and fermentation step (c) are carried out simultaneously or sequentially.

12. The process of any of paragraphs 1-10, comprising
(a) liquefying a starch containing material with an alpha-amylase;
presaccharifying the liquefied material using a carbohydrate-source generating enzyme;
(b) saccharifying in the presence of a cellulolytic composition;
(c) fermenting using a fermentation organism;
wherein saccharification step (b) and fermentation step (c) are carried out simultaneously or sequentially.

13. The process of any of paragraphs 1-12, wherein the presaccharification is carried out at a temperature from 40-75° C., such as 50-70° C., preferably 60° C.; a pH between 4-6, preferably 5; for a period of 30-360 minutes, such as from 60-420 minutes, such as around between 150-180 minutes.

14. The process of any of paragraphs 1-13, wherein the carbohydrate-source generating enzyme and/or the cellulolytic composition are added during saccharification step (b) and/or fermentation step (c), or simultaneous saccharification and fermentation (SSF).

15. The process of any of paragraphs 1-14, comprising
(a) liquefying a starch containing material with an alpha-amylase;
(b) saccharifying the liquefied material in the presence of a carbohydrate-source generating enzyme and a cellulolytic composition;
(c) fermenting using a fermentation organism;
wherein saccharification step (b) and fermentation step (c) are carried out simultaneously or sequentially.

16. The process of any of paragraphs 1-15, wherein the hemicellulase content in the cellulolytic composition constitutes less than 10 wt. % such as less than 5 wt. % of the cellulolytic composition.

17. The process of any of paragraphs 1-16, wherein the beta-glucosidase is from a strain of *Aspergillus*, such as a strain of *Aspergillus fumigatus*, such as *Aspergillus fumigatus* beta-glucosidase (SEQ ID NO: 6 herein), which comprises one or more substitutions selected from the group consisting of L89M, G91L, F100D, 1140V, I186V, S283G, N456E, and F512Y; such as a variant thereof with the following substitutions:
F100D+S283G+N456E+F512Y;
L89M+G91L+I186V+I140V;
I186V+L89M+G91L+I140V+F100D+S283G+N456E+F512Y.

18. The process of any of paragraphs 1-17, wherein the parent beta-glucosidase has at least 60% identity, such as at least 70%, such as at least 80%, such as at least 90%, such as at least 95%, such as at least 96%, such as at least 97%, such as at least 98%, such as at least 99% identity to SEQ ID NO: 6 herein.

19. The process of any of paragraphs 1-18, wherein the beta-glucosidase variant has at least 60% identity, such as at least 70%, such as at least 80%, such as at least 90%, such as at least 95%, such as at least 96%, such as at least 97%, such as at least 98%, such as at least 99%, but less than 100% identity to SEQ ID NO: 6 herein.

20. The process of any of paragraphs 1-19, wherein one or more cellobiohydrolases (CBHs) are present during fermentation, such as a cellobiohydrolase I and/or a cellobiohydrolase II.

21. The process of claim 20, wherein the cellobiohydrolase I (CBH I) is one derived from a strain of the genus *Aspergillus*, such as a strain of *Aspergillus fumigatus*, such as the Cel7a CBHI disclosed in SEQ ID NO: 2 herein, or a strain of the genus *Trichoderma*, such as a strain of *Trichoderma reesei*.

22. The process of any paragraphs 1-21, wherein the cellobiohydrolase II (CBH II) is one derived from a strain of the genus *Aspergillus*, such as a strain of *Aspergillus fumigatus*; such as the one disclosed as SEQ ID NO: 4 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

23. The process of any of paragraphs 1-23 wherein the cellulolytic composition is derived from *Trichoderma reesei* and further comprising one or more of:

(i) an *Aspergillus fumigatus* cellobiohydrolase I, preferably the one shown in SEQ ID NO: 2 herein;
(ii) an *Aspergillus fumigatus* cellobiohydrolase II, preferably the one shown in SEQ ID NO: 4 herein;
(iii) an *Aspergillus fumigatus* beta-glucosidase variant thereof with the following substitutions: F100D, S283G, N456E, F512Y (using SEQ ID NO: 6 herein for numbering).

24. The process of any of paragraphs 1-23, wherein a trehalase is present or adding during fermentation, presacharification, or simultaneous or sequential saccharification and fermentation.

25. The process of paragraph 23, wherein the trehalase is derived from *Trichoderma*, such as *Trichoderma reesei*, such as the *Trichoderma reesei* trehalase shown in SEQ ID NO: 12 herein.

26. The process of paragraphs 24 or 25, wherein the trehalase is present or added in an amount of 5-1,000 micro g/g DS, such as 7-500 micro g/g DS, such as 10-250 micro g/g DS.

27. The process of any of paragraphs 1-26, wherein saccharification and fermentation are carried out sequentlially or simultaneously.

28. The process of any of paragraphs 1-27, further comprising recovering the fermentation product, preferably by distillation, by separate the fermentation material into the liquid fraction (i.e., fermentation product), such as ethanol, and solid fraction (i.e., whole stillage).

29. The process of paragraph 28, further wherein the solid fraction (i.e., whole stillage) is dewatered and separating into a solid phase (i.e., wet cake) and a liquid phase (Thin Stillage), e.g., by centrifugation.

30. The process of any of paragraphs 1-29, comprising
(a) liquefying a starch containing material with an alpha-amylase;
(b) saccharifying the liquefied material using a carbohydrate source generating enzyme;
(c) fermenting using a fermentation organism in the presence of a cellulolytic composition comprising one or more polypeptides selected from the group consisting of:
   GH61 polypeptide having cellulolytic enhancing activity,
   beta-glucosidase;
   Cellobiohydrolase I;
   Cellobiohydrolase II;
or a mixture of two, three, or four thereof.

31. The process of paragraph 30, wherein the cellulolytic composition is derived from *Trichoderma reesei*, *Humicola insolens* or *Chrysosporium lucknowense*.

32. The process of any of paragraph 1-31, wherein the cellulolytic composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 6 herein or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*.

33. The process of any of paragraphs 1-32, wherein the cellulolytic composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 8 herein.

34. The process of any of paragraphs 1-33, wherein the cellulolytic composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 6 in WO 2011/057140 or SEQ ID NO: 2 herein, or a strain of the genus *Trichoderma*, such as a strain of *Trichoderma reesei*.

35. The process of any of paragraphs 1-34, wherein the cellulolytic composition comprises a cellobiohydrolase II (CBH II, such as one derived from a strain of the genus *Aspergillus*, such as a strain of *Aspergillus fumigatus*; such as the one disclosed as SEQ ID NO: 4 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

36. The process of any of paragraphs 1-35, wherein the cellulolytic composition comprises a GH61 polypeptide having cellulolytic enhancing activity and a beta-glucosidase.

37. The process of any of paragraphs 1-36, wherein the cellulolytic composition comprises a GH61 polypeptide having cellulolytic enhancing activity and a beta-glucosidase.

38. The process of any of paragraphs 1-37, wherein the cellulolytic composition comprises a GH61 polypeptide having cellulolytic enhancing activity, a beta-glucosidase, and a CBHI.

39. The process of any of paragraphs 1-38, wherein the cellulolytic composition comprises a GH61 polypeptide having cellulolytic enhancing activity, a beta-glucosidase, a CBHI, and a CBHII.

40. The process of any of paragraphs 1-39, wherein the cellulolytic composition is a *Trichoderma reesei* cellulolytic composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

41. The process of any of paragraphs 1-40, wherein the cellulolytic composition is a *Trichoderma reesei* cellulolytic composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 6 herein.

42. The process of any of paragraphs 1-41, wherein the cellulolytic composition is a *Trichoderma reesei* cellulolytic composition further comprising *Penicillium emersonii* GH61A polypeptide having cellulolytic enhancing activity disclosed in WO 2011/041397 (SEQ ID NO: 8 herein) and *Aspergillus fumigatus* beta-glucosidase (SEQ ID NO: 2 of WO 2005/047499) or SEQ ID NO: 6 herein or a variant thereof with the following substitutions: F100D, S283G, N456E, F512Y.

43. The process of any of paragraphs 1-42, wherein the cellulolytic composition comprises one or more of the following components
(i) an *Aspergillus fumigatus* cellobiohydrolase I;
(ii) an *Aspergillus fumigatus* cellobiohydrolase II;

(iii) an *Aspergillus fumigatus* beta-glucosidase or variant thereof; and
(iv) a *Penicillium* sp. GH61 polypeptide having cellulolytic enhancing activity; or homologs thereof.

44. The process of any of paragraphs 1-43, wherein the cellulolytic composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

45. The process of any of paragraphs 1-44, wherein the alpha-amylase used during liquefaction step (a) is of bacterial origin, such as derived from a strain of the genus *Bacillus*, especially a strain of *Bacillus stearothermophilus* (or *Geobacillus stearothermophilus*), in particular the *Bacillus stearothermophilus* as disclosed in WO 99/019467 as SEQ ID NO: 3 with the double deletion I181+G182 and substitution N193F.

46. The process of any of paragraphs 1-45, wherein the carbohydrate-source generating enzyme is a glucoamylase, such as a glucoamylase of fungal origin, preferably from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of Pycnoporus, or a strain of Gloephyllum, or a strain of the Nigrofomes.

47. The process of any of paragraphs 1-46, wherein the *Aspergillus fumigatus* cellobiohydrolase I or homolog thereof is selected from the group consisting of:
(i) a cellobiohydrolase I comprising the mature polypeptide of SEQ ID NO: 2 herein;
(ii) a cellobiohydrolase I comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 2 herein;
(iii) a cellobiohydrolase I encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 1 herein; and
(iv) a cellobiohydrolase I encoded by a polynucleotide that hybridizes under at least high stringency conditions, e.g., very high stringency conditions, with the mature polypeptide coding sequence of SEQ ID NO: 1 herein or the full-length complement thereof.

48. The process of any of paragraphs 1-47, wherein the *Aspergillus fumigatus* cellobiohydrolase II or homolog thereof is selected from the group consisting of:
(i) a cellobiohydrolase II comprising the mature polypeptide of SEQ ID NO: 4 herein;
(ii) a cellobiohydrolase II comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 4 herein;
(iii) a cellobiohydrolase II encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 3 herein; and
(iv) a cellobiohydrolase II encoded by a polynucleotide that hybridizes under at least high stringency conditions, e.g., very high stringency conditions, with the mature polypeptide coding sequence of SEQ ID NO: 3 herein or the full-length complement thereof.

49. The process of any of paragraphs 1-48, wherein the *Aspergillus fumigatus* beta-glucosidase or homolog thereof is selected from the group consisting of:
(i) a beta-glucosidase comprising the mature polypeptide of SEQ ID NO: 6 herein;
(ii) a beta-glucosidase comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 6 herein;
(iii) a beta-glucosidase encoded by a polynucleotide comprising a nucleotide sequence having at least 70%, e.g., at least 75%, at least 80%, at least 85%, at least 90%, at least 91%, at least 92%, ar least 93%, at least 94%, at least 95%, at least 96%, at least 97%, at least 98%, or at least 99% identity to the mature polypeptide coding sequence of SEQ ID NO: 5 herein; and
(iv) a beta-glucosidase encoded by a polynucleotide that hybridizes under at least high stringency conditions, e.g., very high stringency conditions, with the mature polypeptide coding sequence of SEQ ID NO: 5 herein or the full-length complement thereof.

50. The process of any of paragraphs 1-49, wherein the beta-glucosidase variant comprises a substitution at one or more positions corresponding to positions 100, 283, 456, and 512 of the mature polypeptide of SEQ ID NO: 6 herein, wherein the variant has beta-glucosidase activity.

51. The process of any of paragraphs 1-50, wherein the parent beta-glucosidase of the variant is (a) a polypeptide comprising the mature polypeptide of SEQ ID NO: 6 herein; (b) a polypeptide having at least 80% sequence identity to the mature polypeptide of SEQ ID NO: 6 herein; (c) a polypeptide encoded by a polynucleotide that hybridizes under high or very high stringency conditions with (i) the mature polypeptide coding sequence of SEQ ID NO: 5 herein, (ii) the cDNA sequence contained in the mature polypeptide coding sequence of SEQ ID NO: 5 herein, or (iii) the full-length complementary strand of (i) or (ii); (d) a polypeptide encoded by a polynucleotide having at least 80% identity to the mature polypeptide coding sequence of SEQ ID NO: 5 herein or the cDNA sequence thereof; or (e) a fragment of the mature polypeptide of SEQ ID NO: 6 herein, which has beta-glucosidase activity.

52. The process of any of paragraphs 50 or 51, wherein the beta-glucosidase variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

53. The process of any of paragraphs 50-52, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 6 herein.

54. The process of any of paragraphs 50-53, wherein the number of substitutions is between 1 and 4, such as 1, 2, 3, or 4 substitutions.
55. The process of any of paragraphs 50-54, wherein the variant comprises a substitution at a position corresponding to position 100, a substitution at a position corresponding to position 283, a substitution at a position corresponding to position 456, and/or a substitution at a position corresponding to position 512.
56. The process of any of paragraphs 50-55, wherein the variant comprises Phe100Asp, Ser283Gly, Asn456Glu, Phe512Tyr in SEQ ID NO: 6 herein.
57. The process of any of paragraphs 1-56, wherein the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.
58. The process of any of paragraphs 1-57, wherein the *Penicillium* sp. GH61 polypeptide having cellulolytic enhancing activity or homolog thereof is selected from the group consisting of:
(i) a GH61 polypeptide having cellulolytic enhancing activity comprising the mature polypeptide of SEQ ID NO: 8 herein;
(ii) a GH61 polypeptide having cellulolytic enhancing activity comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 8 herein;
(iii) a GH61 polypeptide having cellulolytic enhancing activity encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 7 herein; and
(iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 herein or the full-length complement thereof.
59. The process of any of paragraphs 1-58, which further comprises one or more enzymes selected from the group consisting of a cellulase, a GH61 polypeptide having cellulolytic enhancing activity, an esterase, an expansin, a laccase, a ligninolytic enzyme, a pectinase, a peroxidase, a protease, and a swollenin.
60. The process of paragraph 59, wherein the cellulase is one or more enzymes selected from the group consisting of an endoglucanase, a cellobiohydrolase, and a beta-glucosidase.
61. The process of paragraph 60, wherein the endoglucanase is an endoglucanase I.
62. The process of paragraph 60, wherein the endoglucanase is an endoglucanase II.
63. The process of any of paragraphs 1-62, wherein saccharification and fermentation are carried out separately or simultaneously.
64. The process of any of paragraphs 1-63, wherein the hemicellulase content in the cellulolytic composition constitutes less than 10 wt. % such as less than 5 wt. % of the cellulolytic composition.
65. A process of producing a fermentation product, comprising
(a) saccharifying the liquefied material using a carbohydrate source generating enzyme and cellulolytic composition;
(b) fermenting using a fermentation organism.
66. The process of paragraph 65, wherein the cellulolytic composition is derived from *Trichoderma reesei, Humicola insolens* or *Chrysosporium lucknowense*.
67 The process of paragraph 65 or 66, wherein the cellulolytic composition comprising a beta-glucosidase, a cellobiohydrolase, and an endoglucanase.
68. The process of any of paragraphs 65-67, wherein the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.
69. The process of any of paragraphs 65-68, wherein the carbohydrate-source generating enzyme is a glucoamylase, preferably a combination of glucoamylase and alpha-amylase.
70. The process of paragraph 69, wherein the glucoamylase is of fungal origin, preferably from a strain of *Aspergillus*, preferably *A. niger, A. awamori*, or *A. oryzae*; or a strain of *Trichoderma*, preferably *T. reesei*; or a strain of *Talaromyces*, preferably *T. emersonii*.
71. The process of paragraph 69 or 70, wherein the alpha-amylase is derived from a strain of the genus *Rhizomucor*, preferably a strain the Rhizomucorpusillus, or the genus *Meripilus*, preferably a strain of *Meripilus giganteus*.
72. The process of any of paragraphs 65-71, wherein the beta-glucosidase is from a strain of *Aspergillus*, such as a strain of *Aspergillus fumigatus*, such as *Aspergillus fumigatus* beta-glucosidase (SEQ ID NO: 6 herein), which comprises one or more substitutions selected from the group consisting of L89M, G91L, F100D, I140V, I186V, S283G, N456E, and F512Y; or a variant thereof with the following substitutions:
F100D+S283G+N456E+F512Y;
L89M+G91L+I186V+I140V;
I186V+L89M+G91L+I140V+F100D+S283G+N456E+F512Y.
73. The process of any of paragraphs 65-72, wherein the beta-glucosidase has at least 60% identity, such as at least 70%, such as at least 80%, such as at least 90%, such as at least 95%, such as at least 96%, such as at least 97%, such as at least 98%, such as at least 99% identity to SEQ ID NO: 6 herein.
74. The process of any of paragraphs 65-73, wherein the beta-glucosidase variant has at least 60% identity, such as at least 70%, such as at least 80%, such as at least 90%, such as at least 95%, such as at least 96%, such as at least 97%, such as at least 98%, such as at least 99%, but less than 100% identity to SEQ ID NO: 6 herein.
75. The process of any of paragraphs 65-74, wherein one or more cellobiohydrolases (CBHs) are present during fermentation, such as a cellobiohydrolase I and/or a cellobiohydrolase II.
76. The process of paragraph 75, wherein the cellobiohydrolase I (CBH I) is one derived from a strain of the genus *Aspergillus*, such as a strain of *Aspergillus fumigatus*, such as the Cel7a CBHI disclosed in SEQ ID NO: 26 in WO 2011/057140 or SEQ ID NO: 2 herein, or a strain of the genus *Trichoderma*, such as a strain of *Trichoderma reesei*.
77. The process of any paragraphs 65-76, wherein the cellobiohydrolase II (CBH II) is one derived from a strain of the genus *Aspergillus*, such as a strain of *Aspergillus fumigatus*; such as the one disclosed as SEQ ID NO: 4 herein or a strain of the genus *Trichoderma*, such as *Trichoderma*

*reesei*, or a strain of the genus *Thielavia*, such as a strain of *Thielavia terrestris*, such as cellobiohydrolase II CEL6A from *Thielavia terrestris*.

78. The process of any of paragraphs 65-77 wherein the cellulolytic composition is derived from *Trichoderma reesei* and further comprising one or more of:
(i) an *Aspergillus fumigatus* cellobiohydrolase I, preferably the one shown in SEQ ID NO: 2 herein;
(ii) an *Aspergillus fumigatus* cellobiohydrolase II, preferably the one shown in SEQ ID NO: 4 herein;
(iii) an *Aspergillus fumigatus* beta-glucosidase with the following substitutions: F100D, S283G, N456E, F512Y (using SEQ ID NO: 6 for numbering).

79. The process of any of paragraphs 65-78, wherein a trehalase is present or adding during fermentation or simultaneous or sequential saccharification and fermentation.

80. The process of paragraph 79, wherein the trehalase is derived from *Trichoderma reesei*.

81. The process of paragraph 79 or 80, wherein the trehalase is present or added in an amount of 5-1,000 micro g/g DS, such as 7-500 micro g/g DS, such as 10-250 micro g/g DS.

82 The process of any of paragraphs 65-81, wherein saccharification and fermentation are carried out sequentlially or simultaneously.

83. The process of any of paragraphs 65-82, wherein the hemicellulase content in the cellulolytic composition constitutes less than 10 wt. % such as less than 5 wt. % of the cellulolytic composition.

84. A process of any of paragraphs 65-83, comprising:
(i) saccharifying a starch-containing material with a carbohydrate-source generating enzymes at a temperature below the initial gelatinization temperature; and
(ii) fermenting using a fermentation organism in the presence of a cellulolytic composition comprising one or more polypeptides selected from the group consisting of:
  GH61 polypeptide having cellulolytic enhancing activity;
  beta-glucosidase;
  Cellobiohydrolase I;
  Cellobiohydrolase II;
or a mixture of two, three, or four thereof.

85. The process of paragraph 84, wherein the cellulolytic composition is derived from *Trichoderma reesei, Humicola insolens* or *Chrysosporium lucknowense*.

86. The process of paragraph 84 or 85, wherein the cellulolytic composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or SEQ ID NO: 6 herein or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*.

87. The process of any of paragraphs 84-86, wherein the cellulolytic composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 8 herein.

88. The process of any of paragraphs 84-87, wherein the cellulolytic composition comprises a cellobiohydrolase I (CBH I), such as one derived from a strain of the genus *Aspergillus*, such as a strain of *Aspergillus fumigatus*, such as SEQ ID NO: 2 herein, such as the Cel7a CBHI disclosed in SEQ ID NO: 6 in WO 2011/057140, or a strain of the genus *Trichoderma*, such as a strain of *Trichoderma reesei*.

89. The process of any of paragraphs 84-88, wherein the cellulolytic composition comprises a cellobiohydrolase II (CBH II, such as one derived from a strain of the genus *Aspergillus*, such as a strain of *Aspergillus fumigatus*, such as SEQ ID NO: 4 herein; or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

90. The process of any of paragraphs 84-89, wherein the cellulolytic composition comprises a GH61 polypeptide having cellulolytic enhancing activity and a beta-glucosidase.

91. The process of any of paragraphs 84-90, wherein the cellulolytic composition comprises a GH61 polypeptide having cellulolytic enhancing activity and a beta-glucosidase.

92. The process of any of paragraphs 84-91, wherein the cellulolytic composition comprises a GH61 polypeptide having cellulolytic enhancing activity, a beta-glucosidase, and a CBHI.

93. The process of any of paragraphs 84-92, wherein the cellulolytic composition comprises a GH61 polypeptide having cellulolytic enhancing activity, a beta-glucosidase, a CBHI, and a CBHII.

94. The process of any of paragraphs 84-93, wherein the cellulolytic composition is a *Trichoderma reesei* cellulolytic composition, further comprising *Thermoascus aurantiacus* GH61A polypeptide having cellulolytic enhancing activity (SEQ ID NO: 2 in WO 2005/074656), and *Aspergillus oryzae* beta-glucosidase fusion protein (WO 2008/057637).

95. The process of any of paragraphs 84-94, wherein the cellulolytic composition is a *Trichoderma reesei* cellulolytic composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499) or SEQ ID NO: 6 herein.

96. The process of any of paragraphs 84-95, wherein the cellulolytic composition is a *Trichoderma reesei* cellulolytic composition further comprising *Penicillium emersonii* GH61A polypeptide having cellulolytic enhancing activity disclosed in WO 2011/041397 and *Aspergillus fumigatus* beta-glucosidase (SEQ ID NO: 2 of WO 2005/047499) or SEQ ID NO: 6 herein or a variant thereof with the following substitutions: F100D, S283G, N456E, F512Y.

97. The process of any of paragraphs 84-96, wherein the cellulolytic composition comprises one or more of the following components
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

98. The process of any of paragraphs 84-97, wherein the cellulolytic composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

99. The process of any of paragraphs 84-98, wherein an alpha-amylase, such as a fungal alpha-amylase, such as an acid fungal alpha-amylase is present during saccharification and/or fermentation.

100. The process of any of paragraphs 84-99, wherein the alpha-amylase activity comes from a fungal alpha-amylase, preferably derived from the genus *Aspergillus*, especially a strain of *Aspergillus niger, Aspergillus oryzae, Aspergillus awamori*, or *Aspergillus kawachii*.

101. The process of any of paragraphs 84-100, wherein the alpha-amylase activity comes from a wild-type alpha-amylase or variant thereof comprising one or more starch binding domains (SBDs).

102. The process of any of paragraphs 84-101, wherein the alpha-amylase activity comes from alpha-amylase derived from a strain of the genus *Rhizomucor*, preferably a strain the *Rhizomucor pusillus*, or the genus *Meripilus*, preferably a strain of *Meripilus giganteus*.

103. The process of any of paragraphs 84-102, wherein the alpha-amylase activity comes from a hybrid alpha-amylase comprising one or more starch binding domains (SBDs).

104. The process of any of paragraphs 84-103, wherein the alpha-amylase is derived from *Rhizomucor pusillus* and has an *Aspergillus niger* glucoamylase linker and SBD or an *Aspergillus kawachii* alpha-amylase linker and SBD.

105. The process of any of paragraphs 84-104, wherein the alpha-amylase activity comes from a hybrid alpha-amylase selected from the group of Fungamyl variant with catalytic domain JA118 and *Athelia rolfsii* SBD, *Rhizomucor pusillus* alpha-amylase with *Athelia rolfsii* glucoamylase linker and SBD, *Meripilus giganteus* alpha-amylase with *Athelia rolfsii* glucoamylase linker and SBD or *Rhizomucor pusillus* alpha-amylase with *Aspergillus niger* glucoamylase linker and SBD.

106. The process of any of paragraphs 84-105, wherein a carbohydrate-source generating enzyme is present during saccharification and/or fermentation.

107. The process of paragraph 106, wherein the carbohydrate-source generating enzyme is a glucoamylase, such as a glucoamylase of fungal origin, such as *Trametes cingulata, Pachykytospora papyracea*; and *Leucopaxillus giganteus* all disclosed in WO 2006/069289; or *Peniophora rufomarginata* disclosed in WO2007/124285; or a mixture thereof.

108. The process of any of paragraphs 84-107, wherein the *Aspergillus fumigatus* cellobiohydrolase I or homolog thereof is selected from the group consisting of:
(i) a cellobiohydrolase I comprising the mature polypeptide of SEQ ID NO: 2 herein;
(ii) a cellobiohydrolase I comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 2 herein;
(iii) a cellobiohydrolase I encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 1 herein; and
(iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

108. The process of any of paragraphs 84-107, wherein the *Aspergillus fumigatus* cellobiohydrolase II or homolog thereof is selected from the group consisting of:
(i) a cellobiohydrolase II comprising the mature polypeptide of SEQ ID NO: 4 herein;
(ii) a cellobiohydrolase II comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 4 herein;
(iii) a cellobiohydrolase II encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 3 herein; and
(iv) a cellobiohydrolase II encoded by a polynucleotide that hybridizes under at least high stringency conditions, e.g., very high stringency conditions, with the mature polypeptide coding sequence of SEQ ID NO: 3 herein or the full-length complement thereof.

109. The process of any of paragraphs 84-108, wherein the *Aspergillus fumigatus* beta-glucosidase or homolog thereof is selected from the group consisting of:
(i) a beta-glucosidase comprising the mature polypeptide of SEQ ID NO: 6 herein;
(ii) a beta-glucosidase comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 6 herein;
(iii) a beta-glucosidase encoded by a polynucleotide comprising a nucleotide sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide coding sequence of SEQ ID NO: 5 herein; and
(iv) a beta-glucosidase encoded by a polynucleotide that hybridizes under at least high stringency conditions, e.g., very high stringency conditions, with the mature polypeptide coding sequence of SEQ ID NO: 5 herein or the full-length complement thereof.

110. The process of any of paragraphs 84-109, wherein the beta-glucosidase variant comprises a substitution at one or more (several) positions corresponding to positions 100, 283, 456, and 512 of the mature polypeptide of SEQ ID NO: 6 herein, wherein the variant has beta-glucosidase activity.

111. The process of any of paragraphs 84-110, wherein the parent beta-glucosidase of the variant is (a) a polypeptide comprising the mature polypeptide of SEQ ID NO: 6 herein; (b) a polypeptide having at least 80% sequence identity to the mature polypeptide of SEQ ID NO: 6 herein; (c) a polypeptide encoded by a polynucleotide that hybridizes under high or very high stringency conditions with (i) the mature polypeptide coding sequence of SEQ ID NO: 5 herein, (ii) the cDNA sequence contained in the mature polypeptide coding sequence of SEQ ID NO: 5 herein, or (iii) the full-length complementary strand of (i) or (ii); (d) a polypeptide encoded by a polynucleotide having at least 80% identity to the mature polypeptide coding sequence of SEQ ID NO: 5 herein or the cDNA sequence thereof; or (e) a fragment of the mature polypeptide of SEQ ID NO: 6 herein, which has beta-glucosidase activity.

112. The process of any of paragraphs 109-111, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

113. The process of any of paragraphs 109-112, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 6 herein.

114. The process of any of paragraphs 109-113, wherein the number of substitutions is between 1 and 4, such as 1, 2, 3, or 4 substitutions.

115. The process of any of paragraphs 109-114, wherein the variant comprises a substitution at a position corresponding to position 100, a substitution at a position corresponding to position 283, a substitution at a position corresponding to position 456, and/or a substitution at a position corresponding to position 512.

116. The process of any of paragraphs 61-66, wherein the variant comprises Phe100Asp, Ser283Gly, Asn456Glu, Phe512Tyr in SEQ ID NO: 6 herein.

117. The process of any of paragraphs 84-116, wherein the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

118. The process of any of paragraphs 84-117, wherein the *Penicillium* sp. GH61 polypeptide having cellulolytic enhancing activity or homolog thereof is selected from the group consisting of:
(i) a GH61 polypeptide having cellulolytic enhancing activity comprising the mature polypeptide of SEQ ID NO: 8 herein;
(ii) a GH61 polypeptide having cellulolytic enhancing activity comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 8 herein;
(iii) a GH61 polypeptide having cellulolytic enhancing activity encoded by a polynucleotide comprising a nucleotide sequence having at least 70%, e.g., at least 75%, at least 80%, at least 85%, at least 90%, at least 91%, at least 92%, at least 93%, at leas 94%, at least 95%, at least 96%, at least 97%, at least 98%, or at least 99% identity to the mature polypeptide coding sequence of SEQ ID NO: 7 herein; and
(iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 herein or the full-length complement thereof.

119. The process of paragraph 118, which further comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

120. The process of paragraph 119, wherein the cellulase is one or more enzymes selected from the group consisting of an endoglucanase, a cellobiohydrolase, and a beta-glucosidase.

121. The process of paragraph 120, wherein the endoglucanase is an endoglucanase I.

122. The process of paragraph 120, wherein the endoglucanase is an endoglucanase II.

123. The process of any of paragraphs 84-122, wherein the cellulolytic composition comprising one or more of the following components:
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

124. The process of any of paragraphs 84-123, wherein saccharification and fermentation are done separately or simultaneously (i.e., as a single step process).

125. The process of any of paragraphs 84-124, wherein the fermentation product is recovered after fermentation.

126. The process of any of paragraphs 84-125, wherein the starch-containing material is plant material selected from the corn (maize), cobs, wheat, barley, rye, milo, sago, cassava, tapioca, sorghum, rice, peas, beans, sweet potatoes, or a mixture thereof, preferably corn.

127. The process of any of paragraphs 84-126, wherein the starch-containing material is granular starch.

128. The process of any of paragraphs 84-1271, wherein the process is carried out at a pH in the range between 3 and 7, preferably from 3 to 6, or more preferably from 3.5 to 5.0.

129. The process of any of paragraphs 84-128, wherein the dry solid content (DS) lies in the range from 20-55 wt.-%, preferably 25-45 wt.-%, more preferably 30-40 wt.-% or 30-45 wt-%.

130. The process of any of paragraphs 84-1293, wherein the sugar concentration is kept at a level below about 6 wt.-%, preferably 3 wt.-%, during saccharification and fermentation, especially below 0.25 wt.-%.

131. The process of any of paragraphs 84-130, wherein a slurry comprising starch-containing material reduced in particle size and water, is prepared before step (a).

132. The process of any of paragraphs 84-131, wherein the starch-containing material is prepared by reducing the particle size of the starch-containing material, preferably by milling, such that at least 50% of the starch-containing material has a particle size of 0.1-0.5 mm.

133. The process of any of paragraphs 84-132, wherein the starch-containing plant material is reduced in particle size, such by dry or wet milling or using particle size emulsion technology.

134. The process of any of paragraphs 84-133, wherein the fermentation is carried out for 30 to 150 hours, preferably 48 to 96 hours.

135. The process of any of paragraphs 84-134, wherein the temperature during fermentation in step (b) or simultaneous saccharification and fermentation in steps (i) and (ii) is between 25° C. and 40° C., preferably between 28° C. and 36° C., such as between 28° C. and 35° C., such as between 28° C. and 34° C., such as around 32° C.

136. The process of any of paragraphs 84-135, wherein further a protease is present during saccharification and/or fermentation.

137. The process of any of paragraphs 84-136, wherein backset is added before and/or during saccharification and/or fermentation.

138. The process of any of paragraphs 84-137, wherein a nitrogen source is added to before and/or during saccharification and/or fermentation.

139. The process of any of paragraphs 84-138, wherein glucoamylase is present in an amount of 0.001 to 10 AGU/g DS, preferably from 0.01 to 5 AGU/g DS, especially 0.1 to 0.5 AGU/g DS.

140. The process of any of paragraphs 84-139, wherein the fermentation product is an alcohol, preferably ethanol, especially fuel ethanol, potable ethanol and/or industrial ethanol.

141. The process of any of paragraphs 84-140, wherein the hemicellulase content in the cellulolytic composition constitutes less than 10 wt. % such as less than 5 wt. % of the cellulolytic composition.

142. The process of any of paragraphs 1-141, wherein the protease is derived from *Thermoascus aurantiacus* CGMCC No. 0670 (classified as EC 3.4.24.39) (disclosed below in the "Protease"-section and shown in SEQ ID NO: 13 herein) or proteases being at least 60%, such as at least 70%, such as at least 80%, such as at least 90%, such as at least 95%, such as at least 96%, such as at least 97%, as as at least 98%, such as at least 99% identical to SEQ ID NO: 13 herein.

143. The process of any of paragraphs 1-142, wherein the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

144. The process of any of paragraphs 1-143, wherein the fermenting organism is derived from a strain of *Saccharomyces*, such as *Saccharomyces cerevisae*.

145. A methods of dewatering whole stillage comprising
(a) liquefying a starch-containing material with an alpha-amylase;
optionally pre-saccharifying the liquefied material before step (b);
(b) saccharifying the liquefied material;
(c) fermenting using a fermentation organism;
(d) separating the fermented material into a fermentation product and whole stillage;
(e) dewatering the whole stillage;
wherein a carbohydrate-source generating enzyme and/or a cellulolytic composition are present or added during the optional presaccharification step, saccharification step (b), and/or fermentation step (c), or simultaneous saccharification and fermentation.

146. The method of paragraph 145, wherein steps (a)-(c) are carried out as defined in paragraphs 1-144.

147. The method of paragraph 145 or 146, wherein the fermentation product is recovered from the fermented material by distillation.

148. The method of any of claims 145-147, wherein the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

149. The method of any of paragraphs 145-148, wherein the cellulolytic composition is adding in from 1-500, such as 10-400, such as 25-300, such as 50-200 micro g/g DS.

150. The method of any of paragraphs 145-149, wherein a protease, such as one derived from *Thermoascus aurantiacus*, or a proteases being at least 60%, such as at least 70%, such as at least 80%, such as at least 90%, such as at least 95%, such as at least 96%, such as at least 97%, as as at least 98%, such as at least 99% identical to SEQ ID NO: 13 herein, is added together with the carbohydrate source generating enzymes and cellulolytic composition.

151. The method of any of paragraphs 145-150, wherein the cellulolytic composition is added directly to the whole stillage.

152. The method of paragraphs 151, comprising the steps of:
i) subjecting whole stillage to a cellulolytic composition, such as the enzymes defined in any of paragraphs 2-64;
ii) separating the material into a solid fraction and a liquid fraction.

153. The method of any of paragraphs 145-152, wherein the fermenting organism is derived from a strain of *Saccharomyces*, such as *Saccharomyces cerevisae*.

The invention claimed is:

1. A process for producing a fermentation product from a starch-containing material comprising the steps of:
   i) liquefying the starch-containing material at a temperature above the initial gelatinization temperature using an alpha-amylase;
   ii) saccharifying using a glucoamylase;
   iii) fermenting using a yeast fermenting organism to produce the fermentation product; and
   wherein a cellulolytic composition derived from a strain of *Trichoderma*, a strain of *Humicola*, or a strain of *Chrysosporium*, and comprising an endoglucanase, a beta-glucosidase, and a cellobiohydrolase is added during saccharification or fermentation.

2. The process of claim 1, wherein the pH during liquefaction is from 4-7.

3. The process of claim 1, wherein liquefying step i) is performed at a temperature between 70-95 degrees centigrade.

4. The process of claim 1, wherein ii) saccharifying and iii) fermentation are done simultaneously.

5. The process of claim 1, wherein the yeast is a *Saccharomyces* sp. yeast.

6. The process of claim 1, wherein the yeast is a *Saccharomyces cerevisiae* yeast.

7. The process of claim 1, wherein the cellobiohydrolase is cellobiohydrolase I (CBHI).

8. The process of claim 1, wherein the cellobiohydrolase is a cellobiohydrolase II (CBHII).

9. The process of claim 1, further wherein a trehalase is added during saccharification or fermentation.

10. The process of claim 1, wherein the starch-containing material is corn.

11. The process of claim 1, wherein the fermentation product is ethanol.

12. The process of claim 11, wherein the ethanol yield is increased compared to the ethanol yield obtained without the cellulolytic composition.

* * * * *

SEQUENCE LISTING

```
<160> NUMBER OF SEQ ID NOS: 13

<210> SEQ ID NO 1
<211> LENGTH: 1599
<212> TYPE: DNA
<213> ORGANISM: Aspergillus fumigatus

<400> SEQUENCE: 1
atgctggcct ccaccttctc ctaccgcatg tacaagaccg cgctcatcct ggccgccctt      60
ctgggctctg gccaggctca gcaggtcggt acttcccagg cggaagtgca tccgtccatg     120
acctggcaga gctgcacggc tggcggcagc tgcaccacca caacggcaa ggtggtcatc      180 gacgcgaact ggcgttgggt gcacaaagtc ggcgactaca ccaactgcta caccggcaac     240
acctgggaca cgactatctg ccctgacgat gcgacctgcg catccaactg cgcccttgag     300
ggtgccaact acgaatccac ctatggtgtg accgccagcg gcaattccct ccgcctcaac     360
ttcgtcacca ccagccagca gaagaacatt ggctcgcgtc tgtacatgat gaaggacgac     420
tcgacctacg agatgtttaa gctgctgaac caggagttca ccttcgatgt cgatgtctcc     480
aacctcccct gcggtctcaa cggtgctctg tactttgtcg ccatggacgc cgacggtggc     540
```

-continued

```
atgtccaagt acccaaccaa caaggccggt gccaagtacg gtactggata ctgtgactcg    600
cagtgccctc gcgacctcaa gttcatcaac ggtcaggcca acgtcgaagg gtggcagccc    660
tcctccaacg atgccaatgc gggtaccggc aaccacgggt cctgctgcgc ggagatggat    720
atctgggagg ccaacagcat ctccacggcc ttcaccccccc atccgtgcga cacgcccggc    780
caggtgatgt gcaccggtga tgcctgcggt ggcacctaca gctccgaccg ctacggcggc    840
acctgcgacc ccgacggatg tgatttcaac tccttccgcc agggcaacaa gaccttctac    900
ggccctggca tgaccgtcga caccaagagc aagtttaccg tcgtcaccca gttcatcacc    960
gacgacggca cctccagcgg caccctcaag gagatcaagc gcttctacgt gcagaacggc   1020
aaggtgatcc ccaactcgga gtcgacctgg accggcgtca gcggcaactc catcaccacc   1080
gagtactgca ccgcccagaa gagcctgttc caggaccaga acgtcttcga aaagcacggc   1140
ggcctcgagg gcatgggtgc ctgccctcgcc cagggtatgg ttctcgtcat gtccctgtgg   1200
gatgatcact cggccaacat gctctggctc gacagcaact acccgaccac tgcctcttcc   1260
accactcccg gcgtcgcccg tggtacctgc gacatctcct ccggcgtccc tgcggatgtc   1320
gaggcgaacc accccgacgc ctacgtcgtc tactccaaca tcaaggtcgg ccccatcggc   1380
tcgaccttca acagcggtgg ctcgaacccc ggtggcggaa ccaccacgac aactaccacc   1440
cagcctacta ccaccacgac cacggctgga aaccctggcg gcaccggagt cgcacagcac   1500
tatggccagt gtggtggaat cggatggacc ggacccacaa cctgtgccag cccttatacc   1560
tgccagaagc tgaatgatta ttactctcag tgcctgtag                          1599
```

<210> SEQ ID NO 2
<211> LENGTH: 532
<212> TYPE: PRT
<213> ORGANISM: Aspergillus fumigatus

<400> SEQUENCE: 2

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

```
Tyr Gly Thr Gly Tyr Cys Asp Ser Gln Cys Pro Arg Asp Leu Lys Phe
            195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
            275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
            355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
            435                 440                 445

Val Val Tyr Ser Asn Ile Lys Val Gly Pro Ile Gly Ser Thr Phe Asn
    450                 455                 460

Ser Gly Gly Ser Asn Pro Gly Gly Thr Thr Thr Thr Thr Thr Thr Thr
465                 470                 475                 480

Gln Pro Thr Thr Thr Thr Thr Ala Gly Asn Pro Gly Gly Thr Gly Thr
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
            515                 520                 525

Ser Gln Cys Leu
530

<210> SEQ ID NO 3
<211> LENGTH: 1713
<212> TYPE: DNA
<213> ORGANISM: Aspergillus fumigatus

<400> SEQUENCE: 3
atgaagcacc ttgcatcttc catcgcattg actctactgt tgcctgccgt gcaggcccag      60
cagaccgtat ggggccaatg tatgttctgg ctgtcactgg aataagactg tatcaactgc     120
tgatatgctt ctaggtggcg gccaaggctg gtctggcccg acgagctgtg ttgccggcgc     180
```

-continued

```
agcctgtagc acactgaatc cctgtatgtt agatatcgtc ctgagtggag acttatactg    240
acttccttag actacgctca gtgtatcccg ggagccaccg cgacgtccac caccctcacg    300
acgacgacgg cggcgacgac gacatcccag accaccacca aacctaccac gactggtcca    360
actacatccg cacccaccgt gaccgcatcc ggtaacccct tcagcggcta ccagctgtat    420
gccaacccct actactcctc cgaggtccat actctggcca tgccttctct gcccagctcg    480
ctgcagccca aggctagtgc tgttgctgaa gtgccctcat ttgtttggct gtaagtggcc    540
ttatcccaat actgagacca actctctgac agtcgtagcg acgttccgc caaggtgccc     600 actatgggaa cctacctggc cgacattcag gccaagaaca aggccggcgc caaccctcct    660
atcgctggta tcttcgtggt ctacgacttg ccggaccgtg actgcgccgc tctggccagt    720
aatggcgagt actcaattgc caacaacggt gtggccaact acaaggcgta cattgacgcc    780
atccgtgctc agctggtgaa gtactctgac gttcacacca tcctcgtcat cggtaggccg    840
tacacctccg ttgcgcgccg ccttcctctg acatcttgca gaacccgaca gcttggccaa    900
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc cgccgcaaca ctcttcgcca agtctacac    1140 cgacgcgggt tcccccgcgg ctgttcgtgg cctggccacc aacgtcgcca actacaacgc   1200
ctggtcgctc agtacctgcc cctcctacac ccagggagac cccaactgcg acgagaagaa   1260
gtacatcaac gccatggcgc ctcttctcaa ggaagccggc ttcgatgccc acttcatcat   1320
ggatacctgt aagtgcttat ccaatcgcc gatgtgtgcc gactaatcaa tgtttcagcc    1380
cggaatggcg tccagcccac gaagcaaaac gcctggggtg actggtgcaa cgtcatcggc   1440
accggcttcg tgttcgccc tcgactaac accggcgatc cgctccagga tgcctttgtg     1500
tggatcaagc ccggtggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713
```

<210> SEQ ID NO 4
<211> LENGTH: 454
<212> TYPE: PRT
<213> ORGANISM: Aspergillus fumigatus

<400> SEQUENCE: 4

```
Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95
```

-continued

```
Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450
```

<210> SEQ ID NO 5
<211> LENGTH: 3060
<212> TYPE: DNA
<213> ORGANISM: Aspergillus fumigatus

<400> SEQUENCE: 5

```
atgagattcg gttggctcga ggtggccgct ctgacggccg cttctgtagc caatgcccag      60
gtttgtgatg ctttcccgtc attgtttcgg atatagttga caatagtcat ggaaataatc     120
aggaattggc tttctctcca ccattctacc cttcgccttg ggctgatggc cagggagagt     180
gggcagatgc ccatcgacgc gccgtcgaga tcgtttctca gatgacactg gcggagaagg     240
ttaaccttac aacgggtact gggtgggttg cgactttttt gttgacagtg agctttcttc     300
actgaccatc tacacagatg ggaaatggac cgatgcgtcg gtcaaaccgg cagcgttccc     360
aggtaagctt gcaattctgc aacaacgtgc aagtgtagtt gctaaaacgc ggtggtgcag     420
acttggtatc aactggggtc tttgtggcca ggattcccct ttgggtatcc gtttctgtga     480
gctatacccg cggagtcttt cagtccttgt attatgtgct gatgattgtc tctgtatagc     540
tgacctcaac tccgccttcc ctgctggtac taatgtcgcc gcgacatggg acaagacact     600
cgcctacctt cgtggcaagg ccatgggtga ggaattcaac gacaagggcg tggacatttt     660
gctggggcct gctgctggtc ctctcggcaa atacccggac ggcggcagaa tctgggaagg     720
cttctctcct gatccggttc tcactggtgt acttttcgcc gaaactatca agggtatcca     780
agacgcgggt gtgattgcta ctgccaagca ttacattctg aatgaacagg agcatttccg     840
acaggttggc gaggcccagg gatatggtta caacatcacg gagacgatca gctccaacgt     900
ggatgacaag accatgcacg agttgtacct tggtgagta gttgacactg caaatgagga      960
ccttgattga tttgactgac ctggaatgca ggccctttgc agatgctgtg cgcggtaaga    1020
ttttccgtag acttgacctc gcgacgaaga atcgctgac gaaccatcgt agctggcgtt     1080
ggcgctgtca tgtgttccta caatcaaatc aacaacagct acggttgtca aaacagtcaa    1140
actctcaaca agctcctcaa ggctgagctg gccttccaag gcttcgtcat gagtgactgg    1200
agcgctcacc acagcggtgt cggcgctgcc ctcgctgggt tggatatgtc gatgcctgga    1260
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt cccctaact tcagctcctg gacccgggat      1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctgggggtagt ggtactgcca acttcccctta ccttgtcacc    1740
cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg aagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
```

-continued

```
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccct cctgaaggct ggcggcgctc ctggtggtaa ccctacccctt    2700 tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca aaagtaccc caagaaagtg    3000 cacgtcggca gctcctcgcg taagctgcct ctgagagcgc ctctgccccg tgtctactag    3060
```

<210> SEQ ID NO 6
<211> LENGTH: 863
<212> TYPE: PRT
<213> ORGANISM: Aspergillus fumigatus

<400> SEQUENCE: 6

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255
```

```
Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670
```

| | | | | | | | | | | | |
|---|---|---|---|---|---|---|---|---|---|---|---|
| Ser | Ala | Tyr | Val | Pro | Thr | Ser | Gly | Glu | Thr | Lys | Pro | Ala | Pro | Thr | Tyr |
| | | | 675 | | | | 680 | | | | 685 | | | | |

Ser Ala Tyr Val Pro Thr Ser Gly Glu Thr Lys Pro Ala Pro Thr Tyr
            675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705             710                 715                 720

Asp Ser Ser Asp Asp Pro Asn Tyr Gly Trp Glu Asp Ser Glu Tyr Ile
            725                 730                 735

Pro Glu Gly Ala Arg Asp Gly Ser Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785             790                 795                 800

Arg Lys Phe Asp Arg Ile Phe Leu Ala Pro Gly Glu Gln Lys Val Trp
            805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
            850                 855                 860

<210> SEQ ID NO 7
<211> LENGTH: 835
<212> TYPE: DNA
<213> ORGANISM: Penicillium sp.

<400> SEQUENCE: 7

```
atgctgtctt cgacgactcg caccctcgcc tttacaggcc ttgcgggcct tctgtccgct      60
cccctggtca aggcccatgg ctttgtccag ggcattgtca tcggtgacca attgtaagtc     120
cctctcttgc agttctgtcg attaactgct ggactgcttg cttgactccc tgctgactcc     180
caacagctac agcgggtaca tcgtcaactc gttccctac gaatccaacc cacccccgt       240
catcggctgg ccacgaccg ccaccgacct gggcttcgtc gacggcacag gataccaagg      300
cccggacatc atctgccacc ggaatgcgac gcccgcgccg ctgacagccc ccgtggccgc     360
cggcggcacc gtcgagctgc agtggacgcc gtggccggac agccaccacg gacccgtcat     420
cacctacctg cgccgtgca acggcaactg ctcgaccgtc gacaagacga cgctggagtt     480
cttcaagatc gaccagcagg gcctgatcga cgacacgagc ccgccgggca cctgggcgtc     540
ggacaacctc atcgccaaca caatagctg gaccgtcacc attcccaaca gcgtcgcccc     600
cggcaactac gtcctgcgcc acgagatcat cgccctgcac tcggccaaca acaaggacgg     660
cgcccagaac taccccagt gcatcaacat cgaggtcacg gcggcggct ccgacgcgcc       720
tgagggtact ctgggcgagg atctctacca tgacaccgac ccgggcattc tggtcgacat     780
ttacgagccc attgcgacgt ataccattcc ggggccgcct gagccgacgt tctag          835
```

<210> SEQ ID NO 8
<211> LENGTH: 253
<212> TYPE: PRT
<213> ORGANISM: Penicillium sp.

```
<220> FEATURE:
<221> NAME/KEY: SIGNAL
<222> LOCATION: (1)..(25)
<220> FEATURE:
<221> NAME/KEY: SIGNAL
<222> LOCATION: (26)..(253)

<400> SEQUENCE: 8
```

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

```
<210> SEQ ID NO 9
<211> LENGTH: 618
<212> TYPE: PRT
<213> ORGANISM: Talaromyces emersoonii
<220> FEATURE:
<221> NAME/KEY: SIGNAL
<222> LOCATION: (1)..(20)
<220> FEATURE:
<221> NAME/KEY: mat_peptide
<222> LOCATION: (21)..(618)

<400> SEQUENCE: 9
```

Met Ala Ser Leu Val Ala Gly Ala Leu Cys Ile Leu Gly Leu Thr Pro
-20                 -15                 -10                 -5

Ala Ala Phe Ala Arg Ala Pro Val Ala Ala Arg Ala Thr Gly Ser Leu
            -1  1               5                   10

Asp Ser Phe Leu Ala Thr Glu Thr Pro Ile Ala Leu Gln Gly Val Leu
            15                  20                  25

-continued

```
Asn Asn Ile Gly Pro Asn Gly Ala Asp Val Ala Gly Ala Ser Ala Gly
 30              35                  40
Ile Val Val Ala Ser Pro Ser Arg Ser Asp Pro Asn Tyr Phe Tyr Ser
 45                  50                  55                  60
Trp Thr Arg Asp Ala Ala Leu Thr Ala Lys Tyr Leu Val Asp Ala Phe
                 65                  70                  75
Ile Ala Gly Asn Lys Asp Leu Glu Gln Thr Ile Gln Gln Tyr Ile Ser
             80                  85                  90
Ala Gln Ala Lys Val Gln Thr Ile Ser Asn Pro Ser Gly Asp Leu Ser
         95                 100                 105
Thr Gly Gly Leu Gly Glu Pro Lys Phe Asn Val Asn Glu Thr Ala Phe
    110                 115                 120
Thr Gly Pro Trp Gly Arg Pro Gln Arg Asp Gly Pro Ala Leu Arg Ala
125                 130                 135                 140
Thr Ala Leu Ile Ala Tyr Ala Asn Tyr Leu Ile Asp Asn Gly Glu Ala
                145                 150                 155
Ser Thr Ala Asp Glu Ile Ile Trp Pro Ile Val Gln Asn Asp Leu Ser
            160                 165                 170
Tyr Ile Thr Gln Tyr Trp Asn Ser Ser Thr Phe Asp Leu Trp Glu Glu
        175                 180                 185
Val Glu Gly Ser Ser Phe Phe Thr Thr Ala Val Gln His Arg Ala Leu
    190                 195                 200
Val Glu Gly Asn Ala Leu Ala Thr Arg Leu Asn His Thr Cys Ser Asn
205                 210                 215                 220
Cys Val Ser Gln Ala Pro Gln Val Leu Cys Phe Leu Gln Ser Tyr Trp
                225                 230                 235
Thr Gly Ser Tyr Val Leu Ala Asn Phe Gly Ser Gly Arg Ser Gly
            240                 245                 250
Lys Asp Val Asn Ser Ile Leu Gly Ser Ile His Thr Phe Asp Pro Ala
        255                 260                 265
Gly Gly Cys Asp Asp Ser Thr Phe Gln Pro Cys Ser Ala Arg Ala Leu
    270                 275                 280
Ala Asn His Lys Val Val Thr Asp Ser Phe Arg Ser Ile Tyr Ala Ile
285                 290                 295                 300
Asn Ser Gly Ile Ala Glu Gly Ser Ala Val Ala Val Gly Arg Tyr Pro
                305                 310                 315
Glu Asp Val Tyr Gln Gly Gly Asn Pro Trp Tyr Leu Ala Thr Ala Ala
            320                 325                 330
Ala Ala Glu Gln Leu Tyr Asp Ala Ile Tyr Gln Trp Lys Lys Ile Gly
        335                 340                 345
Ser Ile Ser Ile Thr Asp Val Ser Leu Pro Phe Phe Gln Asp Ile Tyr
    350                 355                 360
Pro Ser Ala Ala Val Gly Thr Tyr Asn Ser Gly Ser Thr Thr Phe Asn
365                 370                 375                 380
Asp Ile Ile Ser Ala Val Gln Thr Tyr Gly Asp Gly Tyr Leu Ser Ile
                385                 390                 395
Val Glu Lys Tyr Thr Pro Ser Asp Gly Ser Leu Thr Glu Gln Phe Ser
            400                 405                 410
Arg Thr Asp Gly Thr Pro Leu Ser Ala Ser Ala Leu Thr Trp Ser Tyr
        415                 420                 425
Ala Ser Leu Leu Thr Ala Ser Ala Arg Arg Gln Ser Val Val Pro Ala
    430                 435                 440
```

-continued

```
Ser Trp Gly Glu Ser Ser Ala Ser Ser Val Pro Ala Val Cys Ser Ala
445                 450                 455                 460

Thr Ser Ala Thr Gly Pro Tyr Ser Thr Ala Thr Asn Thr Val Trp Pro
            465                 470                 475

Ser Ser Gly Ser Gly Ser Ser Thr Thr Ser Ser Ala Pro Cys Thr
                480                 485                 490

Thr Pro Thr Ser Val Ala Val Thr Phe Asp Glu Ile Val Ser Thr Ser
            495                 500                 505

Tyr Gly Glu Thr Ile Tyr Leu Ala Gly Ser Ile Pro Glu Leu Gly Asn
        510                 515                 520

Trp Ser Thr Ala Ser Ala Ile Pro Leu Arg Ala Asp Ala Tyr Thr Asn
525                 530                 535                 540

Ser Asn Pro Leu Trp Tyr Val Thr Val Asn Leu Pro Pro Gly Thr Ser
                545                 550                 555

Phe Glu Tyr Lys Phe Phe Lys Asn Gln Thr Asp Gly Thr Ile Val Trp
            560                 565                 570

Glu Asp Asp Pro Asn Arg Ser Tyr Thr Val Pro Ala Tyr Cys Gly Gln
        575                 580                 585

Thr Thr Ala Ile Leu Asp Asp Ser Trp Gln
    590                 595
```

<210> SEQ ID NO 10
<211> LENGTH: 574
<212> TYPE: PRT
<213> ORGANISM: Trametes cingulata
<220> FEATURE:
<221> NAME/KEY: SIGNAL
<222> LOCATION: (1)..(18)
<220> FEATURE:
<221> NAME/KEY: mat_peptide
<222> LOCATION: (19)..(574)

<400> SEQUENCE: 10

```
Met Arg Phe Thr Leu Leu Thr Ser Leu Leu Gly Leu Ala Leu Gly Ala
                -15                 -10                 -5

Phe Ala Gln Ser Ser Ala Ala Asp Ala Tyr Val Ala Ser Glu Ser Pro
    -1  1               5                   10

Ile Ala Lys Ala Gly Val Leu Ala Asn Ile Gly Pro Ser Gly Ser Lys
15                  20                  25                  30

Ser Asn Gly Ala Lys Ala Gly Ile Val Ile Ala Ser Pro Ser Thr Ser
                35                  40                  45

Asn Pro Asn Tyr Leu Tyr Thr Trp Thr Arg Asp Ser Ser Leu Val Phe
            50                  55                  60

Lys Ala Leu Ile Asp Gln Phe Thr Thr Gly Glu Asp Thr Ser Leu Arg
        65                  70                  75

Thr Leu Ile Asp Glu Phe Thr Ser Ala Glu Ala Ile Leu Gln Gln Val
    80                  85                  90

Pro Asn Pro Ser Gly Thr Val Ser Thr Gly Gly Leu Gly Glu Pro Lys
95                  100                 105                 110

Phe Asn Ile Asp Glu Thr Ala Phe Thr Asp Ala Trp Gly Arg Pro Gln
                115                 120                 125

Arg Asp Gly Pro Ala Leu Arg Ala Thr Ala Ile Ile Thr Tyr Ala Asn
            130                 135                 140

Trp Leu Leu Asp Asn Lys Asn Thr Thr Tyr Val Thr Asn Thr Leu Trp
        145                 150                 155

Pro Ile Ile Lys Leu Asp Leu Asp Tyr Val Ala Ser Asn Trp Asn Gln
    160                 165                 170
```

```
Ser Thr Phe Asp Leu Trp Glu Glu Ile Asn Ser Ser Phe Phe Thr
175                 180                 185                 190

Thr Ala Val Gln His Arg Ala Leu Arg Glu Gly Ala Thr Phe Ala Asn
            195                 200                 205

Arg Ile Gly Gln Thr Ser Val Val Ser Gly Tyr Thr Thr Gln Ala Asn
            210                 215                 220

Asn Leu Leu Cys Phe Leu Gln Ser Tyr Trp Asn Pro Thr Gly Gly Tyr
            225                 230                 235

Ile Thr Ala Asn Thr Gly Gly Arg Ser Gly Lys Asp Ala Asn Thr
240                 245                 250

Val Leu Thr Ser Ile His Thr Phe Asp Pro Ala Ala Gly Cys Asp Ala
255                 260                 265                 270

Val Thr Phe Gln Pro Cys Ser Asp Lys Ala Leu Ser Asn Leu Lys Val
            275                 280                 285

Tyr Val Asp Ala Phe Arg Ser Ile Tyr Ser Ile Asn Ser Gly Ile Ala
            290                 295                 300

Ser Asn Ala Ala Val Ala Thr Gly Arg Tyr Pro Glu Asp Ser Tyr Met
            305                 310                 315

Gly Gly Asn Pro Trp Tyr Leu Thr Thr Ser Ala Val Ala Glu Gln Leu
320                 325                 330

Tyr Asp Ala Leu Ile Val Trp Asn Lys Leu Gly Ala Leu Asn Val Thr
335                 340                 345                 350

Ser Thr Ser Leu Pro Phe Phe Gln Gln Phe Ser Ser Gly Val Thr Val
            355                 360                 365

Gly Thr Tyr Ala Ser Ser Ser Thr Phe Lys Thr Leu Thr Ser Ala
            370                 375                 380

Ile Lys Thr Phe Ala Asp Gly Phe Leu Ala Val Asn Ala Lys Tyr Thr
            385                 390                 395

Pro Ser Asn Gly Gly Leu Ala Glu Gln Tyr Ser Arg Ser Asn Gly Ser
400                 405                 410

Pro Val Ser Ala Val Asp Leu Thr Trp Ser Tyr Ala Ala Ala Leu Thr
415                 420                 425                 430

Ser Phe Ala Ala Arg Ser Gly Lys Thr Tyr Ala Ser Trp Gly Ala Ala
            435                 440                 445

Gly Leu Thr Val Pro Thr Thr Cys Ser Gly Ser Gly Gly Ala Gly Thr
            450                 455                 460

Val Ala Val Thr Phe Asn Val Gln Ala Thr Thr Val Phe Gly Glu Asn
            465                 470                 475

Ile Tyr Ile Thr Gly Ser Val Pro Ala Leu Gln Asn Trp Ser Pro Asp
480                 485                 490

Asn Ala Leu Ile Leu Ser Ala Ala Asn Tyr Pro Thr Trp Ser Ile Thr
495                 500                 505                 510

Val Asn Leu Pro Ala Ser Thr Thr Ile Glu Tyr Lys Tyr Ile Arg Lys
            515                 520                 525

Phe Asn Gly Ala Val Thr Trp Glu Ser Asp Pro Asn Asn Ser Ile Thr
            530                 535                 540

Thr Pro Ala Ser Gly Thr Phe Thr Gln Asn Asp Thr Trp Arg
            545                 550                 555

<210> SEQ ID NO 11
<211> LENGTH: 583
<212> TYPE: PRT
<213> ORGANISM: Rhizomucor pusillus
```

-continued

```
<220> FEATURE:
<221> NAME/KEY: misc_feature
<223> OTHER INFORMATION: Rhizomucor pusillus alpha-amylase with
      Aspergillus niger glucoamylase linker and SBD

<400> SEQUENCE: 11

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
        290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380
```

```
Gly Ser Gly Ser Thr Asn Gln Val Ser Phe Val Ser Gly Lys Phe
385                 390                 395                 400

Asp Ser Gly Ala Ser Leu Met Asp Ile Val Ser Asn Ile Thr Thr Thr
            405                 410                 415

Val Ser Ser Asp Gly Thr Val Thr Phe Asn Leu Lys Asp Gly Leu Pro
        420                 425                 430

Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
    450                 455                 460

Ser Lys Thr Ser Thr Ser Thr Ser Thr Ser Cys Thr Thr Pro Thr
465                 470                 475                 480

Ala Val Ala Val Thr Phe Asp Leu Thr Ala Thr Thr Thr Tyr Gly Glu
            485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
    530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 12
<211> LENGTH: 661
<212> TYPE: PRT
<213> ORGANISM: Trichoderma reesei
<220> FEATURE:
<221> NAME/KEY: mat_peptide
<222> LOCATION: (1)..(661)

<400> SEQUENCE: 12

Leu Tyr Ile Asn Gly Ser Val Ile Ala Pro Cys Asp Ser Pro Ile Tyr
1               5                   10                  15

Cys His Gly Asp Ile Leu Arg Glu Ile Glu Leu Ala His Pro Phe Ser
            20                  25                  30

Asp Ser Lys Thr Phe Val Asp Met Pro Ala Lys Arg Pro Leu Ser Glu
        35                  40                  45

Ile Gln Thr Ala Phe Ala Asn Leu Pro Lys Pro Leu Arg Asn Asp Ser
    50                  55                  60

Ser Leu Gln Thr Phe Leu Ala Ser Tyr Phe Ala Asp Ala Gly Gly Glu
65                  70                  75                  80

Leu Ile Gln Val Pro Arg Ala Asn Leu Thr Thr Asn Pro Thr Phe Leu
            85                  90                  95

Ser Lys Ile Asn Asp Thr Val Ile Glu Gln Phe Val Thr Gln Val Ile
            100                 105                 110

Asp Ile Trp Pro Asp Leu Thr Arg Arg Tyr Ala Gly Asp Ala Ala Val
        115                 120                 125

Lys Asn Cys Ser Ser Cys Pro Asn Ser Phe Ile Pro Val Asn Arg Thr
    130                 135                 140

Phe Val Val Ala Gly Gly Arg Phe Arg Glu Pro Tyr Tyr Trp Asp Ser
145                 150                 155                 160
```

```
Tyr Trp Ile Val Glu Gly Leu Leu Arg Thr Gly Ala Phe Val Gly
                165                 170                 175
Ile Ala Arg Asn Thr Ile Asp Asn Phe Leu Asp Phe Ile Glu Arg Phe
            180                 185                 190
Gly Phe Val Pro Asn Gly Ala Arg Leu Tyr Tyr Leu Asn Arg Ser Gln
            195                 200                 205
Pro Pro Leu Leu Ser Arg Met Val Lys Val Tyr Ile Asp His Thr Asn
            210                 215                 220
Asp Thr Ala Ile Leu Arg Arg Ala Leu Pro Leu Val Lys Glu His
225                 230                 235                 240
Glu Phe Trp Thr Arg Asn Arg Thr Val Asp Val Arg Val Asn Asn Lys
                245                 250                 255
Thr Tyr Val Leu Asn Gln Tyr Ala Val Gln Asn Thr Gln Pro Arg Pro
            260                 265                 270
Glu Ser Phe Arg Glu Asp Phe Gln Thr Ala Asn Asn Arg Ser Tyr Tyr
            275                 280                 285
Ala Ala Ser Gly Ile Ile Tyr Pro Ala Thr Lys Pro Leu Asn Glu Ser
            290                 295                 300
Gln Ile Glu Glu Leu Tyr Ala Asn Leu Ala Ser Gly Ala Glu Ser Gly
305                 310                 315                 320
Asn Asp Tyr Thr Ala Arg Trp Leu Ala Asp Pro Ser Asp Ala Met Arg
                325                 330                 335
Asp Val Tyr Phe Pro Leu Arg Ser Leu Asn Asn Lys Asp Ile Val Pro
            340                 345                 350
Val Asp Leu Asn Ser Ile Leu Tyr Gly Asn Glu Leu Ala Ile Ala Gln
            355                 360                 365
Phe Tyr Asn Gln Thr Gly Asn Thr Thr Ala Ala Arg Glu Trp Ser Ser
            370                 375                 380
Leu Ala Ala Asn Arg Ser Ala Ser Ile Gln Ala Val Phe Trp Asn Glu
385                 390                 395                 400
Thr Leu Phe Ser Tyr Phe Asp Tyr Asn Leu Thr Ser Ser Ser Gln Asn
                405                 410                 415
Ile Tyr Val Pro Leu Asp Lys Asp Ala Val Ala Leu Asp Arg Gln Thr
            420                 425                 430
Ala Pro Pro Gly Lys Gln Val Leu Phe His Val Gly Gln Phe Tyr Pro
            435                 440                 445
Phe Trp Thr Gly Ala Ala Pro Glu Tyr Leu Arg Asn Asn Pro Phe Ala
            450                 455                 460
Val Thr Arg Ile Phe Asp Arg Val Lys Ser Tyr Leu Asp Thr Arg Pro
465                 470                 475                 480
Gly Gly Ile Pro Ala Ser Asn Val Asn Thr Gly Gln Gln Trp Asp Gln
                485                 490                 495
Pro Asn Val Trp Pro Pro His Met His Ile Leu Met Glu Ser Leu Asn
            500                 505                 510
Ser Val Pro Ala Thr Phe Ser Glu Ala Asp Pro Ala Tyr Gln Asp Val
            515                 520                 525
Arg Asn Leu Ser Leu Arg Leu Gly Gln Arg Tyr Leu Asp Phe Thr Phe
            530                 535                 540
Cys Thr Trp Arg Ala Thr Gly Gly Ser Thr Ser Glu Thr Pro Lys Leu
545                 550                 555                 560
Gln Gly Leu Thr Asp Gln Asp Val Gly Ile Met Phe Glu Lys Tyr Asn
                565                 570                 575
```

```
Asp Asn Ser Thr Asn Ala Ala Gly Gly Gly Glu Tyr Gln Val Val
            580             585             590

Glu Gly Phe Gly Trp Thr Asn Gly Val Leu Leu Trp Thr Ala Asp Thr
        595             600             605

Phe Gly Ser Gln Leu Lys Arg Pro Gln Cys Gly Asn Ile Met Ala Gly
        610             615             620

His Pro Ala Pro Ser Lys Arg Ser Ala Val Gln Leu Asp Met Trp Asp
625             630             635             640

Ala Ser Arg Val Lys Lys Phe Gly Arg Arg Ala Glu Gly Arg Met Gly
            645             650             655

Thr Leu His Ala Trp
            660

<210> SEQ ID NO 13
<211> LENGTH: 177
<212> TYPE: PRT
<213> ORGANISM: Thermoascus authatiacus

<400> SEQUENCE: 13

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
            35                  40                  45

Ser Ser Thr Arg Gln Thr Val Ala Ala Arg Leu Arg Ala Val Ala Arg
        50                  55                  60

Glu Ala Ser Ser Ser Ser Gly Ala Thr Thr Tyr Tyr Cys Asp Asp
65              70                  75                  80

Pro Tyr Gly Tyr Cys Ser Ser Asn Val Leu Ala Tyr Thr Leu Pro Ser
            85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
            115                 120                 125

Glu Phe Thr His Ala Pro Gly Val Tyr Ser Pro Gly Thr Asp Asp Leu
        130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
            165                 170                 175

Cys
```